US009125971B2

(12) United States Patent
Wolfinbarger, Jr. et al.

(10) Patent No.: US 9,125,971 B2
(45) Date of Patent: *Sep. 8, 2015

(54) PLASTICIZED BONE AND SOFT TISSUE GRAFTS AND METHODS OF MAKING AND USING SAME

(71) Applicant: LifeNet Health, Virginia Beach, VA (US)

(72) Inventors: Lloyd Wolfinbarger, Jr., Virginia Beach, VA (US); Robert K. O'Leary, Deltaville, VA (US); Billy G. Anderson, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/836,803

(22) Filed: Mar. 15, 2013

(65) Prior Publication Data

US 2013/0218294 A1    Aug. 22, 2013

Related U.S. Application Data

(60) Continuation of application No. 12/701,634, filed on Feb. 8, 2010, which is a continuation of application No. 11/053,454, filed on Feb. 9, 2005, now abandoned, which is a continuation of application No. 09/940,545, filed on Aug. 29, 2001, now abandoned, which is a division of application No. 09/107,459, filed on Jun. 30, 1998, now Pat. No. 6,293,970.

(51) Int. Cl.
*A61F 2/28* (2006.01)
*A61L 27/36* (2006.01)
*A61F 2/46* (2006.01)
*A61L 27/50* (2006.01)
*A61F 2/02* (2006.01)
*A61F 2/30* (2006.01)

(52) U.S. Cl.
CPC .............. *A61L 27/362* (2013.01); *A61F 2/02* (2013.01); *A61F 2/4644* (2013.01); *A61L 27/365* (2013.01); *A61L 27/3608* (2013.01); *A61L 27/3683* (2013.01); *A61L 27/502* (2013.01); *A61F 2002/2825* (2013.01); *A61F 2002/2835* (2013.01); *A61F 2002/2839* (2013.01); *A61F 2002/30535* (2013.01); *A61F 2002/4646* (2013.01); *A61F 2002/4649* (2013.01); *A61F 2250/0058* (2013.01); *A61L 2430/02* (2013.01)

(58) Field of Classification Search
USPC .......... 623/11.11, 16.11, 23.51, 23.58, 23.59, 623/23.61, 23.63; 424/422, 423; 435/1.2, 435/1.3
See application file for complete search history.

(56) References Cited

U.S. PATENT DOCUMENTS

| | | |
|---|---|---|
| 3,458,397 A | 7/1969 | Myers et al. |
| 4,278,701 A | 7/1981 | Von Hagens |
| 4,357,274 A | 11/1982 | Werner |
| 4,539,716 A | 9/1985 | Bell |
| 4,546,500 A | 10/1985 | Bell |
| 4,678,470 A | 7/1987 | Nashef et al. |
| 4,776,853 A | 10/1988 | Klement et al. |
| 4,801,299 A | 1/1989 | Brendel et al. |
| 4,810,299 A | 3/1989 | Schilling et al. |
| 4,835,102 A | 5/1989 | Bell et al. |
| 4,846,835 A | 7/1989 | Grande |
| 4,950,296 A | 8/1990 | McIntyre |
| 4,969,912 A | 11/1990 | Kelman et al. |
| 5,061,286 A | 10/1991 | Lyle |
| 5,095,925 A | 3/1992 | Elledge et al. |
| 5,116,552 A | 5/1992 | Morita et al. |
| 5,118,512 A | 6/1992 | O'Leary et al. |
| 5,120,833 A | 6/1992 | Kaplan |
| 5,171,273 A | 12/1992 | Silver et al. |
| 5,290,558 A | 3/1994 | O'Leary et al. |

(Continued)

FOREIGN PATENT DOCUMENTS

| | | |
|---|---|---|
| DE | 19513177 A1 | 10/1996 |
| SU | 1175481 | 8/1985 |

(Continued)

OTHER PUBLICATIONS

Osinowo et al., The use of glycerol-preserved homologous dura mater grafts in cardiac surgery: the Southampton experience, The Annals of Thoracic Surgery, Apr. 1985 39(4): 367-70.*
Abstract of Chang, CM, et al., "Swelling of and Drug Release from Monoglyceride-Based Drug Delivery Systems," J Pharm Sci, Jun. 1997, pp. 747-752, vol. 86.
Abstract of Norling, T., et al., "Formulation of a Drug Delivery System Based on a Mixture of Monoglycerides and Triglycerides for Use in the treatment of Periodontal Disease," J Clin Periodontol, Oct. 1992, pp. 687-692, vol. 19.

(Continued)

*Primary Examiner* — Pedro Philogene
*Assistant Examiner* — David C Comstock
(74) *Attorney, Agent, or Firm* — Cahn & Samuels, LLP

(57) ABSTRACT

The present invention provides a plasticized dehydrated or freeze-dried bone and/or soft tissue product that does not require special conditions of storage, for example refrigeration or freezing, exhibits materials properties that approximate those properties present in normal hydrated tissue, is not brittle, does not necessitate rehydration prior to clinical implantation and is not a potential source for disease transmission. The invention replaces water in the molecular structure of the bone or soft tissue matrix with one or more plasticizers allowing for dehydration of the tissue, yet not resulting in an increase in brittleness of the plasticized product, and resulting in compressive and/or tensile properties similar to those of normal hydrated bone. Replacement of the chemical plasticizers by water prior to implantation is not required and thus, the dehydrated bone or soft tissue plasticized product can be placed directly into an implant site without significant preparation in the operating room.

13 Claims, No Drawings

(56) References Cited

U.S. PATENT DOCUMENTS

| | | |
|---|---|---|
| 5,298,254 A | 3/1994 | Prewett et al. |
| 5,333,626 A | 8/1994 | Morse et al. |
| 5,336,616 A | 8/1994 | Livesey et al. |
| 5,352,463 A | 10/1994 | Badylak et al. |
| 5,357,636 A | 10/1994 | Dresdner et al. |
| 5,432,712 A | 7/1995 | Chan |
| 5,466,462 A | 11/1995 | Rosenthal et al. |
| 5,507,813 A | 4/1996 | Dowd et al. |
| 5,513,662 A | 5/1996 | Morse et al. |
| 5,525,646 A | 6/1996 | Lundgren et al. |
| 5,531,791 A | 7/1996 | Wolfinbarger |
| 5,556,379 A | 9/1996 | Wolfinbarger |
| 5,558,875 A | 9/1996 | Wang |
| 5,598,838 A | 2/1997 | Servidio et al. |
| 5,607,476 A | 3/1997 | Prewett et al. |
| 5,613,982 A | 3/1997 | Goldstein |
| 5,632,778 A | 5/1997 | Goldstein |
| 5,716,405 A | 2/1998 | Mittelman |
| 5,718,012 A | 2/1998 | Cavallaro |
| 5,762,600 A | 6/1998 | Bruchman et al. |
| 5,772,439 A | 6/1998 | Yamaoka et al. |
| 5,792,603 A | 8/1998 | Dunkelman et al. |
| 5,797,871 A | 8/1998 | Wolfinbarger, Jr. |
| 5,820,581 A | 10/1998 | Wolfinbarger, Jr. |
| 5,843,180 A | 12/1998 | Jaffe et al. |
| 5,843,181 A | 12/1998 | Jaffe et al. |
| 5,843,182 A | 12/1998 | Goldstein |
| 5,855,610 A | 1/1999 | Vacanti et al. |
| 5,855,617 A | 1/1999 | Orton |
| 5,855,620 A | 1/1999 | Bishopric et al. |
| 5,856,367 A | 1/1999 | Barrows et al. |
| 5,863,531 A | 1/1999 | Naughton et al. |
| 5,885,617 A | 3/1999 | Jordan |
| 5,899,936 A | 5/1999 | Goldstein |
| 5,899,939 A | 5/1999 | Boyce et al. |
| 5,916,266 A | 6/1999 | Yui et al. |
| 5,928,945 A | 7/1999 | Seliktar |
| 5,944,755 A | 8/1999 | Stone |
| 5,976,104 A | 11/1999 | Wolfinbarger, Jr. |
| 5,977,034 A | 11/1999 | Wolfinbarger, Jr. |
| 5,977,432 A | 11/1999 | Wolfinbarger, Jr. |
| 5,993,844 A | 11/1999 | Abraham et al. |
| 5,997,896 A | 12/1999 | Carr, Jr. et al. |
| 6,024,735 A | 2/2000 | Wolfinbarger, Jr. |
| 6,030,635 A | 2/2000 | Gertzman et al. |
| 6,039,762 A | 3/2000 | McKay |
| 6,046,379 A | 4/2000 | Stone et al. |
| 6,060,306 A | 5/2000 | Flatt et al. |
| 6,110,206 A | 8/2000 | Stone |
| 6,110,209 A | 8/2000 | Stone |
| 6,121,042 A | 9/2000 | Peterson et al. |
| 6,123,731 A | 9/2000 | Boyce et al. |
| 6,162,258 A | 12/2000 | Scarborough et al. |
| 6,200,347 B1 | 3/2001 | Anderson et al. |
| 6,241,771 B1 | 6/2001 | Gresser et al. |
| 6,277,555 B1 | 8/2001 | Duran et al. |
| 6,293,970 B1 | 9/2001 | Wolfinbarger, Jr. |
| 6,294,041 B1 | 9/2001 | Boyce et al. |
| 6,294,187 B1 | 9/2001 | Boyce et al. |
| 6,312,474 B1 | 11/2001 | Francis et al. |
| 6,340,477 B1 | 1/2002 | Anderson |
| 6,348,069 B1 | 2/2002 | Vacanti et al. |
| 6,352,708 B1 | 3/2002 | Duran et al. |
| 6,371,992 B1 | 4/2002 | Tanagho et al. |
| 6,376,244 B1 | 4/2002 | Atala |
| 6,379,367 B1 | 4/2002 | Vibe-Hansen et al. |
| 6,379,385 B1 | 4/2002 | Kalas et al. |
| 6,398,811 B1 | 6/2002 | McKay |
| 6,416,995 B1 | 7/2002 | Wolfinbarger |
| 6,428,802 B1 | 8/2002 | Atala |
| 6,432,710 B1 | 8/2002 | Boss, Jr. et al. |
| 6,432,712 B1 | 8/2002 | Wolfinbarger, Jr. |
| 6,436,138 B1 | 8/2002 | Dowd et al. |
| 6,437,018 B1 | 8/2002 | Gertzman et al. |
| 6,448,076 B2 | 9/2002 | Dennis et al. |
| 6,454,804 B1 | 9/2002 | Ferree |
| 6,458,158 B1 | 10/2002 | Anderson et al. |
| 6,479,064 B1 | 11/2002 | Atala |
| 6,482,584 B1 | 11/2002 | Mills et al. |
| 6,488,033 B1 | 12/2002 | Cerundolo |
| 6,544,289 B2 | 4/2003 | Wolfinbarger, Jr. |
| 6,548,297 B1 | 4/2003 | Kuri-Harcuch et al. |
| 6,569,200 B2 * | 5/2003 | Wolfinbarger et al. ..... 623/13.11 |
| 6,582,696 B2 | 6/2003 | Kuri-Harcuch et al. |
| 6,630,001 B2 | 10/2003 | Duran et al. |
| 6,648,919 B2 | 11/2003 | Ferree |
| 6,652,818 B1 | 11/2003 | Mills et al. |
| 6,734,018 B2 | 5/2004 | Wolfinbarger, Jr. |
| 6,743,574 B1 | 6/2004 | Wolfinbarger, Jr. |
| 6,783,556 B1 | 8/2004 | Gabbay |
| 6,855,169 B2 | 2/2005 | Boyer, II et al. |
| 6,872,357 B1 | 3/2005 | Bronshtein et al. |
| 6,902,578 B1 | 6/2005 | Anderson et al. |
| 6,911,212 B2 | 6/2005 | Gertzman et al. |
| 6,942,961 B1 | 9/2005 | Baumgartner |
| 6,958,149 B2 | 10/2005 | Vukicevic et al. |
| 6,962,775 B2 | 11/2005 | Kuri-Harcuch et al. |
| 6,998,135 B1 | 2/2006 | Sunwoo et al. |
| 7,063,726 B2 | 6/2006 | Crouch et al. |
| 7,067,123 B2 | 6/2006 | Gomes et al. |
| 7,108,721 B2 | 9/2006 | Huckle et al. |
| 7,157,428 B2 | 1/2007 | Kusanagi et al. |
| 2001/0004715 A1 | 6/2001 | Duran et al. |
| 2001/0049138 A1 | 12/2001 | Dennis et al. |
| 2001/0055809 A1 | 12/2001 | Mangat |
| 2002/0106625 A1 | 8/2002 | Hung et al. |
| 2002/0192191 A1 | 12/2002 | Kuri-Harcuch et al. |
| 2002/0192197 A1 | 12/2002 | Kuri-Harcuch et al. |
| 2003/0083752 A1 | 5/2003 | Wolfinbarger, Jr. et al. |
| 2003/0087428 A1 | 5/2003 | Wolfinbarger, Jr. et al. |
| 2003/0135284 A1 | 7/2003 | Crouch et al. |
| 2003/0143207 A1 | 7/2003 | Livesey et al. |
| 2003/0185702 A1 | 10/2003 | Burgess et al. |
| 2003/0217415 A1 | 11/2003 | Crouch et al. |
| 2003/0219417 A1 | 11/2003 | Wolfinbarger, Jr. et al. |
| 2004/0037735 A1 | 2/2004 | DePaula et al. |
| 2004/0057936 A1 | 3/2004 | Cheung |
| 2004/0059430 A1 | 3/2004 | Kim et al. |
| 2004/0067582 A1 | 4/2004 | Wolfinbarger, Jr. et al. |
| 2004/0076657 A1 | 4/2004 | Wolfinbarger, Jr. et al. |
| 2004/0219058 A1 | 11/2004 | Shimp et al. |
| 2004/0219182 A1 | 11/2004 | Gomes et al. |
| 2004/0219659 A1 | 11/2004 | Altman et al. |
| 2004/0230303 A1 | 11/2004 | Gomes et al. |
| 2005/0028228 A1 | 2/2005 | McQuillan et al. |
| 2005/0064042 A1 | 3/2005 | Vunjak-Novakovic et al. |
| 2005/0152987 A1 | 7/2005 | Malinin |
| 2005/0196460 A1 | 9/2005 | Malinin |
| 2006/0073592 A1 | 4/2006 | Sun et al. |
| 2006/0074466 A1 | 4/2006 | Malinin |
| 2007/0082057 A1 | 4/2007 | Masinaei et al. |
| 2007/0082058 A1 | 4/2007 | Masinaei et al. |
| 2007/0083270 A1 | 4/2007 | Masinaei et al. |
| 2007/0093896 A1 | 4/2007 | Malinin |
| 2007/0098759 A1 | 5/2007 | Malinin |
| 2007/0135917 A1 | 6/2007 | Malinin |
| 2007/0135918 A1 | 6/2007 | Malinin |
| 2007/0135928 A1 | 6/2007 | Malinin |

FOREIGN PATENT DOCUMENTS

| | | |
|---|---|---|
| WO | 96/14738 A2 | 5/1996 |
| WO | 0113971 | 3/2001 |
| WO | 2005009134 A1 | 2/2005 |

OTHER PUBLICATIONS

Abstract of Wang, LL, et al., "Inhibition of Listeria Monocytogenes by Fatty Acids and Monoglycerides," Appl Environ Microbiol, Feb. 1992, pp. 624-629, vol. 58.

Abstract of Harsanyi, BB., et al., "Hamster Cheek-Pouch Testing of Dental Soft Polymers," J Dent Res, Jun. 1991, pp. 991-996, vol. 70.

Abstract of Ema, M., et al., "Comparative Developmental Toxicity of n-butyl Benzyl Phthalate and di-n-butyl Phthalate in Rats," Arch Environ Contam Toxicol, Feb. 1995, pp. 223-228, vol. 28.

(56) References Cited

OTHER PUBLICATIONS

Abstract of Srivastava, SP, et al., "Testicular Effects of di-n-butyl Phthalate (DBP): Biochemcial and Histopathological Alterations," Arch Toxicol, 1990, pp. 148-152, vol. 64.

Abstract of Thormar, H., et al., "Inactivation of Visna Virus and Other Enveloped Viruses by Free Fatty Acids and Monoglycerides," Ann N Y Acad Sci, Jun. 6, 1994, pp. 464-471, vol. 724.

Abstract of Scriba, GK, et al., "Bioavailability and Anticonvulsant Activity of a Monoglyceride-Derived Prodrug of Phenytoin After Oral Administration to Rats," J Pharm Sci, Mar. 1995, pp. 300-302, vol. 84.

Abstract of Greco, AV, et al., "Toxicity of Disodium Sebacate," Drugs Exp Clin Res, 1990, pp. 531-536, vol. 16.

Kabasawa, Y., et al., "Allergic Contact Dermatitis from Ethyl Sebacate," Contact Dermatitis, Apr. 1990, pp. 226, vol. 22.

Abstract of Bertuzzi, A., et al., "Sebacic Acid Binding to Human Plasma Albumin," Biochem Pharmacol, Feb. 9, 1993, pp. 697-702, vol. 45.

Abstract of Zhang, Q., et al., "The Modification of Hemoglobin by a Long Crosslinking Reagent: Bis(3,5-Dibromosalicyl) Sebacate," Biochem Biophys Res Commun, Sep. 30, 1994, pp. 1463-1470, vol. 203.

Mochida, K, et al., "Acetyl Tributyl Citrate and Dibutyl Sebacate Inhibit the Growth of Cultured Mammalian Cells," Bull Environ Contam Toxicol, Apr. 1996, pp. 635-637, vol. 56.

De Groot, AC, et al., "Contact Allergy to Di-Isopropyl Sebacate in Zineryt Lotion," Contact Dermatitis, Oct. 1991, pp. 260, vol. 25.

Abstract of Mingrone, G., et al., "Kinetics and Thermogenesis of Medium-Chained Monocarboxlyic and Dicarboxylic Acids in Man: Sebacate and Medium-Chain Triglycerides," JPEN J Parenter Enteral Nutr, May-Jun. 1993, pp. 257-264, vol. 17.

Abstract of Atkins, TW, "Fabrication of Microspheres Using Blends of Poly(Ethylene Adipate) and Poly(Ethylene Adipate)/Poly(Hydroxybutyrate-Hydroxyvalerate) with Poly(Caprolactone): Incorporation and Release of Bovine Serum Albumin," J Biomater Sci Polym Ed, 1997, pp. 833-845, vol. 8.

Abstract of Mingrone, G., et al., "Tissue Uptake and Oxidation of Disodium Sebacate in Man," JPEN J Parenter Enteral Nutr, Jul.-Aug. 1991, pp. 454-459, vol. 15.

Abstract of Supuran, CT, et al., "Novel Aromatic/Heterocyclic Sulfonamides and Their Metal Complexes as Inhibitors of Carbonic Anhydrase Isozymes I, II, IV," J Enzyme Inhib, Apr. 1997, pp. 37-51, vol. 12.

Abstract of Petschow, B W, et al., "Susceptibility of Helicobacter Pylori to Bactericidal Properties of Medium-Chain Monoglycerides and Free Fatty Acids," Antimicrob Agents Chemother, Feb. 1996, pp. 302-306, vol. 40.

Abstract of Nishinari, K., et al., "Effect of Sugars and Polyols on Water in Agarose Gels," Adv Exp Med Biol, 1991, pp. 235-249, 302.

Abstract of Kiyosawa, K., et al., "Volumetric Properties of Polyols (Ethylene Glycol, Glycerol, Meso-Erythritol, Xylitol, and Mannitol) in Relation to Their Membrane Permeability: Group Additivity and Estimation of the Maximum Radius of Their Molecules," Biochim Biophys Acta, May 7, 1991, pp. 251-255, vol. 1064.

Abstract of Reddy, VN., et al., "Study of Polyol Pathway and Cell Permeability Changes in Human Lens and Retinal Pigment Epithelium in Tissue Culture," Invest Opthalmol Vis Sci, Jun. 1992, pp. 2334-2339, vol. 33.

Abstract of Utsumi, K., et al., "Cryprotective Effect of Polyols on Rat Embryos During Two-Step Freezing," Cryobiology, Jun. 1992, pp. 332-341, vol. 29.

Abstract of Duncan-Hewitt, WC, et al., "Modeling the Uniaxial Compaction of Pharmaceutical Powders Using the Mechanical Properties of Single Crystals, II: Brittle Materials," J Pharm Sci, Mar. 1990, pp. 273-278, vol. 79.

Abstract of Walker, EM Jr., et al., "Enhanced Mobilization of Hepatic Cadmium in Mice Upon Coadministration of an N, N-Disubstituted Dithiocarbamate and an Alkyl Monoester of Dimercaptosuccinate," Res Commun Chem Pathol Parmacol, Jan. 1992, pp. 121-124, vol. 75.

Russell et al, "The synthesis of 2-O-alkyl-myo-inositol 1-phospates as competitive inhibitors of Inositol Monophosphatase," Carbohydr Res, Oct. 9, 1992, pp. 263-268, vol. 234.

Abstract of Fries, KM, et al., "31P NMR and Chloride Ion Kinetics of Alkylating Mnoester Phophoramidates," J Med Chem, Feb. 1991, pp. 565-569, vol. 34.

Abstract of Boogaard, PJ, et al., "Effects of Exposure to Low Concentrations of Chlorinated Hydrocarbons on the Kidney and Liver of Industrial Workers," Br J Ind Med, Apr. 1993, pp. 331-339, vol. 50.

Abstract of Scheele J., et al., "Chlorinated Hydrocarbons in the Bone Marrow of Children: Studies on Their Association with Leukaemia," Eur J Pediatr, Nov. 1992, pp. 802-805, vol. 151.

Abstract of Moser, U., et al., "Aliphatic and Heterocyclic Analogues of Arecaidine Propargyl Ester. Structure-Activity Relationships of Mono- and Bivalent Ligands at Muscarinic M1 (M4), M2 and M3 Receptor Subtypes," Arzneimittelforschung, Apr. 1995, pp. 449-455, vol. 45.

Abstract of Boogaard, PJ., et al., "Effects of Exposure to Low Concentrations of Chlorinated Hydrocarbons on the Kidney and Liver of Industrial Workers," Br J Ind Med, Apr. 1993, pp. 331-339, vol. 50.

Abstract of Frangos, SA, et al., "Chlorinated Hydrocarbon Solvents: Substituting Our Way Toward Human Carcinogenicity," Am J Ind Med, Oct. 1993, pp. 355-364, vol. 24.

Abstract of McCarty, LP, et al., "Acute toxicity in rats of chlorinated hydrocarbons given via the intratracheal route", Hum Exp Toxicol, May 1992, pp. 173-177, vol. 11.

Abstract of Graham, BS, et al., "An In Vivo and In Vitro Study of the Loss of Plasticizer from Soft Polymer-Gel Materials," J Dent Res., May 1991, pp. 870-873, vol. 70, No. 5.

Abstract of Zieger, MA, et al., "Injury and Protection in Split-Thickness Skin After Very Rapid Cooling and Warming," Cryobiology, Aug. 1997, pp. 53-69, vol. 35.

Abstract of Ensikat, HJ, et al., "Liquid Substitution: A Versatile Procedure for SEM Specimen Preparation of Biological Materials Without Drying or Coating," J Microsc, Dec. 1993, pp. 195-203, vol. 172, pt. 3.

Abstract of Pessoa De Barros, TE, et al., "Plasty of Tendon with Dura Mater. Experimental Study," Arch Orthop Trauma Surg, 1990, pp. 131-132, vol. 109.

Abstract of Hinton, R., et al., "A Biomechanical Analysis of Solvent-Dehydrated and Freeze-Dried Human Fascia Lata Allografts. A Preliminary Report," Am J Sports Med, Sep.-Oct. 1992, pp. 607-612, vol. 20.

Yoshinaga, K., et al., "Protection by Trehalose of DNA from Radiation Damage," Biosci. Biotech. Biochem., 1997, pp. 160-161, vol. 61, No. 1.

Abstract of Ghosh, MM, et al., "A Comparison of Methodologies for the Preparation of Human Epidermal-Dermal Composites," Ann Plast Surg., Oct. 1997, pp. 390-404, vol. 39.

Abstract of Bourroul, SC., et al., "Sterilization of Skin Allografts by Ionizing Radiation," Cell Mol Biol, Nov. 2002, pp. 803-807, vol. 48, No. 7.

Brockbank, K.G.M., et al., "Vitrification: Preservation of Cellular Implants," Topics in Tissue Engineering, 2003, Chapter 12.

Balderson et al., 45th Annual Meeting, Orthopaedic Research Society. (Feb. 1-4, 1999), pp. 785.

H.-H. Sievers, et al., "Decellularized pulmonary homograft (SynerGraft) for reconstruction of the right ventricular outflow tract: first clinical experience" Z. Kardiol, vol. 92, No. 53, 2003.

Robert Madden, et al., "Decellularized Cadaver Vein Allografts Used for Hemodialysis Access Do Not Cause Allosensitization or Preclude Kidney Transplanation" Journal of Kidney Diseases, vol. 40, No. 6, Dec. 2002, pp. 1240-1243.

P.M. Dohmen, et al., "In Vitro hydrodynamics of a decellularized pulmonary procine valve, compared with a glutarldehyde and polyurethane heart valve" Journal of Artificial Organs, vol. 25, No. 11, 2002, pp. 1089-1094.

B. S. Conklin, et al., "Development and evaluation of a novel decellularized vascular xenograft" Medical Engineering and Physics, vol. 24, 2002, pp. 173-183.

J. Clark, et al., "Decellularized Dermal Grafting in Cleft Palate Repair" Facial Plastic Surg., vol. 5, 2003, pp. 40-44.

(56) References Cited

OTHER PUBLICATIONS

Ronald C. Elkins, et al., "Decellularized Human Valve Allofgrafts" Society of Thoracic Surgeons, 2001, pp. S428-S432.

Steven Goldstein, et al., "Transpecies Heart Valve Transplant: Advanced Studies of a Bioengineered Xeno-Autograft" Society of Thoracic Surgeons, 2000, pp. 1963-1969.

Pascal M. Dohmen, et al., "Ross Operation with a Tissue-Engineered Heart Valve" Society of Thoracic Surgeons, 2002, pp. 1438-1442.

David W. Courtman, et al., "Biomechanical and ultrastructural comparison of cryopreservation and a novel cellular extraction of porcine aortic valve leaflets" Journal of Biomedical Materials Research, vol. 29, 1995, pp. 1507-1516.

Gregory Wilson, et al., "Acellular Matrix Allograft Small Caliber Vascular Prostheses" Trans. Am. Sog. Artif. Intern. Organs, 1990, vol. XXXVI, pp. M340-M343.

David W. Courtman, et al., "The Acellular Matrix Vascular Prosthesis: Investigation of its Potential as a Xenograft for Clinical Application" Biomaterial Tissue Interfaces, vol. 10, 1992, pp. 241-246.

David W. Courtman, et al., "Development of a pericardial acellular matrix biomaterial: Biochemical and mechanical effects of cell extraction" Journal of Biomedical Materials Research, vol. 28, 1994, pp. 655-666.

Gregory J. Wilson, et al., "Acellular Matrix: A Biomaterials Approach for Coronary Artery Bypass and Heart Valve Replacement" Society of Thoracic Surgeons, 1995, pp. S353-S358.

Sotiris A. Korrossis, et al., "Tissue Engineering of Cardiac Valve Prostheses II: Biomechanical Characterization of Decellularized Porcine Aortic Heart Valves" Heart Valve Disease, vol. 11, No. 4, Jul. 2002, pp. 463-471.

Lalka et al., "Acellular vascular matrix: A natural endothelial cell substrate" (1989) Annals of Vascular Surgery, vol. 3, No. 2, pp. 108-117.

Bianchi et al., 21st. Annual Meeting. American Association of Tissue Banks. (Aug. 23-27, 1997), p. 48.

Kang et al., "The biomechanical properties of deep freezing and freeze drying bones and their biomechanical changes after in-vivo allograft," Yonsei Medical Journal. vol. 36, No. 4, (1995), pp. 332-335.

Voggenreiter et al., "Effects of preservation and sterilization on cortical bone grafts. A scanning electron microscopic study," Archives of Orthopaedic and Traumatic Surgery, vol. 113. (1994). pp. 294-296.

Pelker, et al., "Biomechanical properties of bone autografts and allografts," Orthopedic Clinics of North America, vol. 18, No. 2, (Apr. 1987). pp. 235-239.

Pelker. et al., "Effects of freezing and freeze-drying on the biomechanical properties of rat bone," Journal of Orthopaedic Research, vol. 1, No. 4, (1984), pp. 405-411.

Pelker. et al., "Biomechanical properties of bone allografts," Clinical Orthopaedics and Related Research, No. 174. (Apr. 1983), pp. 54-57.

Triantafyllou et al., "The mechanical properties of the lyophylized and irradiated bone grafts" Acta Orthopaedica BelQica, vol. 41, Suppl. I. (1975), pp. 35-44.

Jerosch et al., "Effects of various rehydration periods on the stability and water content of bone transplants following freeze-drying, gamma sterilization and lipid extraction" Zeitschrift Orthopadie 132. (1994), pp. 335-341.

Pappas, A .• Cryobiology. vol. 4, No. 6 (1968), pp. 358-375.

Boyne, P. "Review of the literature on cryopreservation of bone" Cryobiology. vol. 4, No. 6 (1968), pp. 341-357.

Kreuz, F., et al .• "The Preservation and Clinical Use of Freeze Dried Bone," J Bone Joint Surg. 1951; 33A: 863.

Schwade, N., "Implants, Soft Tissue, Alloderm," emedicine.com, copyright 2004.

Wolfinbarger, L., Zhang. YI, Adam, BLT., Hornsi, D., Gates, K., and Sutherland, V .• 1994, Biomechanical aspects on rehydrated freeze-dried human allograft dura mater tissues• J. Applied biomaterials, 5:265-270.

Wolfinbarger et al. "A comprehensive study of physical parameters, biomechanical properties, and statistical correlations of iliac crest bone wedges used in spinal fusion surgery. I. Physical parameters and their correlations" Spine 19:277-283 (1994).

Osinowo et al., "The use of glycerol-preserved homologous dura mater grafts in cardiac surgery: the Southhampton experience," The Annals of Thoracic Surgery, 39(4):367-370 (1985).

Wolfinbarger, L., et al., "Biomechancial Aspects on Rehydrated Freeze-Dried Human Allograft Dura Mater Tissues," J. Applied Biomaterials, 1994, pp. 265-270, vol. 5.

Sievers, H.-H., et al., "Decellularized Pulmonary Homograft for Reconstruction of Right Ventricular Outflow Trace: First Clinical Experience," Z. Kardiol, 2003, vol. 92, No. 53.

Madden, Robert, et al., "Decellularized Cadaver Vein Allografts Used for Hemodialysis Access Do Not Cause Allosensitization or Preclude Kidney Transplantation," Journal of Kidney Diseases, 2002, pp. 1240-1243, vol. 40, No. 6.

Dohmen, P.M., et al., "In Vitro Hydrodynamics of a Decellularized Pulmonary Porcine Valve, Compared with a Glutaraldehyde and Polyurethane Heart Valve," Journal of Artificial Organs, 2002, pp. 1089-1094, vol. 25, No. 11.

Conklin, B.S., et al., "Development and Evaluation of a Novel Decellularized Vascular Xenograft," Medical Engineering and physics, 2002, pp. 173-183, vol. 24.

Clark, J., et al., "Decellularized Dermal Grafting in Cleft Palate Repair," Facial Plastic Surg., 2003 pp. 40-44, vol. 5.

Elkins, Ronald C., et al., Decellularized Human Valve Allografts, Society of Thoracic Surgeons, 2001, pp. S428-S432.

Goldstein, Steven, et al., "Transpecies Heart Valve Transplant: Advanced Studies of a Bioengineered Xeno-Autograft," Society of Thoracic Surgeons, 2000, pp. 1963-1969.

Dohmen, Pascal M., et al. "Ross Operation with a Tissue-Engineered Heart Valve," Society of Thoracic Surgeons, 2002, pp. 1438-1442.

Courtman, David W., et al., "Biomechanical and Ultrastructural Comparison of Cryopreservation and a Novel Cellular Extraction of Porcine Aortic Valve Leaflets," Journal of Biomedical Materials Research, 1995, pp. 1507-1516, vol. 29.

Wilson, Gregory, et al., "Acellular Matrix Allograft Small Caliber Vascular Prostheses," Trans. Am. Sog. Artif. Intern. Organs, 1990, pp. M340-M343, vol. XXXVI.

Courtman, David W., et al., "The Acellular Matrix Vascular Prosthesis: Investigation of its Potential as a Xenograft for Clinical Application," Biomaterial Tissues Interfaces, 1992, pp. 241-246, vol. 10.

Courtman, David W., et al., "Development of a Pericardial Acellular Matrix Biomaterial: Biochemical and Mechanical Effects of Cell Extraction," Journal of Biomedical Materials Research, 1994, pp. 655-666, vol. 28.

Wilson, Gregory J., et al., "Acellular Matrix: A Biomaterials Approach for Coronary Artery Bypass and Heart Valve Replacement," Society of Thoracic Surgeons, 1995, pp. S353-S358.

Korrossis, Sotiris A., et al., "Tissue Engineering of Cardiac Valve Prostheses II: Biomechanical Characterization of Decellularized Porcine Aortic Heart Valves," Heart Valve Disease 11, 2002 pp. 463-471.

Kreuz, F., et al., "The Preservation and Clinical Use of Freeze Dried Bone," J Bone Joint Surg., 1951, vol. 33A, No. 863.

Lalka, et al., "Acellular Vascular Matrix: A Natural Endothelial Cell Substrate," Annals of Vascular Surgery, 1989, pp. 108-117, vol. 3, No. 2.

Boyne, P., Cryobiology, 1968, pp. 341-357, vol. 4, No. 6.

Pappas, A., Cryobiology, 1968, pp. 358-375, vol. 4, No. 6.

Triantafyllou, et al., Acta Orthopaedica Belgica, Suppl. 1, 1975, pp. 35-44, vol. 41.

Pelker, et al., Clinical Orthopaedics and Related Research, Apr. 1983, pp. 54-57, No. 174.

Pelker, et al., Journal of Orthopaedic Research, 1984, pp. 405-411, vol. 1, No. 4.

Pelker, et al., Orthopedic Clinics of North America, Apr. 1987, pp. 235-239, vol. 18, No. 2.

Jerosch, et al., Zeitschrift Orthopadie, 1994, pp. 335-341, vol. 132.

Voggenreiter, et al., Archives of Orthopaedic and Traumatic Surgery, 1994, pp. 294-296, vol. 113.

Kang, et al., Yonsei Medical Journal, 1995, pp. 332-335, vol. 36, No. 4.

(56) References Cited

OTHER PUBLICATIONS

Bianchi, et al., 21st Annual Meeting, American Association of Tissue Banks, Aug. 23-27, 1997, pp. 48.
Balderson, et al., 45th Annual Meeting, Orthopaedic Research Society, Feb. 1-4, 1999, pp. 785.
Abstract of Parker, R., et al., "Elasticity of Frozen Aortic Valve Homografts," Cardiovasc Res. Mar. 1977, pp. 156-159, vol. 11, No. 2.
Abstract of Moore, CH., et al., "Analysis of Homograft Valve Failure in 311 Patients Followed Up to 10 Years," Ann Thorac Surg. Sep. 1975, pp. 274-281, vol. 20, No. 3.
Abstract of Ingegneri, A., et al., "An 11-Year Assessment of 93 Flash-Frozen Homograft Valves in the Aortic Position," Thorac Cardiovasc Surg., Oct. 1979, pp. 304-307 vol. 27, No. 5.
Abstract of Bodnar, E., et al., "Long Term Performance of 580 Homograft and Autograft Valves Used for Aortic Valve Replacement," Thorac Cardiovasc Surg., Feb. 1979, pp. 31-38, vol. 27, No. 1.
Ross, DN, "Biologic Vales. Their Performance and Prospects," Circulation, Jun. 1972, pp. 1259-1272, vol. 45, No. 6.
Abstract of Meintjes, J., et al., "Synthetic, Biological and Composite Scaffolds for Abdominal Wall Reconstruction," Expert Rev Med Devices, Mar. 2011, pp. 275-288, vol. 8, No. 2.
Abstract of NG, KW, et al., "In Vitro Characterization of Natural and Synthetic Dermal Matrices Cultured with Human Dermal Fibroblasts," Biomaterials, Jun. 2004, pp. 2807-2818, vol. 25, No. 14.
Abstract of Derwin, KA, et al., "Commercial Extracellular Matrix Scaffolds for Rotator Cuff Tendon Repair. Biomechanical, Biochemical, and Cellular Properties", J Bone Joint Surg Am., Dec. 2006, pp. 2665-2672, vol. 88, No. 12.
Ketchedjian, Ara, et al., "Ovine Panel Reactive Antibody Assay of HLA Responsivity to Allograft Bioengineered Vascular Scaffolds," The Journal of Thoracic and Cardiovascular Surgery, 2004, pp. 159-166, vol. 129, No. 1.
Hopkins, Richard A., et al., "Decellularization Reduces Calcification While Improving Both Durability and 1-Year Functional Results of Pulmonary Homograft Valves in Juvenile Sheep," The Journal of Thoracic and Cardiovascular Surgery, 2009, pp. 907-913, vol. 137, No. 1.
Crapo, Peter M, et al., "An Overview of Tissue and Whole Organ Decellularization Processes," Biomaterials, Apr. 2011, pp. 3233-3243, vol. 32, No. 12.
Parker, R., et al., "Storage of Heart Valve Allografts in Glycerol with Subsequent Antibiotic Sterilisation," Thorax, 1978, pp. 638-645, vol. 33.
Gilbert, Thomas W., et al., "Quantification of DNA in Biologic Scaffold Materials," J Surg Res., Mar. 2009, pp. 135-139, vol. 152, No. 1.
OPTIM Synthetic Glycerine-Freezing Point, The Dow Chemical Company, retrieved from www.dow.com.
Abstract of Aidulis et al., Processing of ovine cardiac allografts: 1. Effects of preservation method on structure and mechanical properties, Cell and Tissue Banking, (2002) vol. 3, No. 2, pp. 79-89.
Anderson, CryoLife Letter (2009), http://www.sec.gov/Archives/edgar/data/784199/000091406210000036/cryolife8k12110ex992.htm.
Ben-Bassat, Hannah, "Performance and Safety of Skin Allograts," Clinics in Dermatology, 2005, pp. 365-375, vol. 23.
Chou, S.K., et al., "Development of a Novel Pressure Swing Adsorption Dehydration System for the Preservation of Dermal Tissue," Materials Science and Engineering C, 2007, pp. 313-324, vol. 27.
De Backere, A. C. J., "Euro Skin Bank: Large Scale Skin-Banking in Europe Based on Glycerol-Preservation of Donor Skin," Burns, 1994, pp. S4-S9, vol. 20, No. 1.
Ge, Liangpeng, et al., "Chapter 13: Skin Graft Preservation," Skin Grafts—Indications, Applications and Current Research, 2011, www.intechopen.com.
Hoekstra, M. J., et al., "History of the Euro Skin Bank: The Innovation of Preservation Technologies," Burns, 1994, pp. S43-S47, vol. 20, No. 1.

Huang, Qizhi, et al., "Banking of Non-Viable Skin Allografts using High Concentrations of Glycerol or Propylene Glycol," Cell and Tissue Banking, 2004, pp. 3-21, vol. 5.
Huang, Qizhi, et al., "Use of Peracetic Acid to Sterilize Human Donor Skin for Production of Acellular Dermal Matrices for Clinical Use," Wound Rep Reg, 2004, pp. 276-287, vol. 12.
Khanna, S. K., et al., "Homograft Aortic Valve Replacement: Seven Years' Experience with Antibotic-Treated Valves," Thorax, 1981, pp. 330-337, vol. 36.
Mackie, David P., "The Euro Skin Bank: Development and Application of Glycerol-Preserved Allograts," J Burn Care Rehabil, 1997, pp. 87-89, vol. 18.
Maral Tugural, et al, "Effectiveness of Human Amnion Preserved Long-Term in Glycerol as a Temporary Biological Dressing," Burns, 1999, pp. 625-635.
Zerbini, E. J., et al., "Result of Replacement of Cardiac Valves by Homologous Dura Mater Valves," Chest, Jun. 1975, vol. 67, No. 6.
Penkova, R., et al., "Stablizing Effect of Glycerol on Collagen Type I Isolated from Different Species," Food Chemistry, 1999, pp. 483-487, vol. 66.
Ravishanker, R., et al, ""Amnion Bank"—The Use of Long Term Glycerol Preserved Amniotic Membranes in the Management of Superficial and Superficial Partial Thickness Burns," Burns, 2003, pp. 369-374, vol. 29.
Basile, M.D., A.R.D., "A Comparative Study of Glycerinized and Lyophilized Porcine Skin in Dressings for Third-Degree Burns", 69 Plastic and Reconstruction Surgery Jun. 6, 1982, pp. 969-972.
Kreis, R. W., et al., "Historical Appraisal of the Use of Skin Allografts in the Treatment of Extension Full Skin Thickness Burns at the Red Cross Hospital Burns Centre, Beverwijk, The Netherlands", Burns, 1992, pp. S19-S22, vol. 18, Supplement 2.
Levin, M.D., L. Scott, "Soft-Tissue Handling", Techniques in Orthopaedics, 1995, pp. 151, vol. 10, No. 2.
May, S. R., et al., "Reduced Bacteria on Transplantable Allograft Skin after Preparation with Chlorhexidine Gluconate, Povidone-Iodine, and Isopropanol", Journal of Burn Care & Rehabilitation, May/Jun. 1991, pp. 224-228, vol. 12, No. 3.
Richters, C. D., et al., "Morphology of Glycerol-Preserved Human Cadaver Skin", Burns, 1996, pp. 113-116, vol. 22, No. 2.
Hettich, R., et al., "The Immunogenicity of Glycerol-Preserved Donor Skin", Burns, 1994, pp. S71-S76, vol. 20, Supplement 1.
McKay, I., et al., "Reconstruction of Human Skin from Glycerol-Preserved Allodermis and Cultured Keratinocyte Sheets", Burns, 1994, pp. S19-S22, vol. 20, No. 1.
Hermans, M. H. E., "Clinical Experience with Glycerol-Preserved Donor Skin Treatment in Partial Thickness Burns", Burns, 1989, pp. 57-59, vol. 15, No. 1.
Van Baare, J., et al., "Microbiological Evaluation of Glycerolized Cadaveric Donor Skin", Transplantation, Apr. 15, 1998, pp. 966-970, vol. 65, No. 7.
Van Baare, J., et al., "Virucidal Effect of Glycerol as Used in Donor Skin Preservation", Burns, 1994, pp. S77-S80, vol. 20, No. 1.
Kreis, R. W., et al., "The Use of Non-Viable Glycerol-Preserved Cadaver Skin Combined with Widely Expanded Autografts in the Treatment of Extensive Third-Degree Burns," The Journal of Trauma, Jan. 1989, pp. 51-54, vol. 29, No. 1.
Richters, C. D., et al., "Immunogenicity of Glycerol-Preserved Human Cadaver Skin in Vitro", Journal of Burn Care & Rehabilitation, May-Jun. 1997, pp. 228-233, vol. 18, No. 3.
Langdon, R. C., et al., "Reconstitution of Structure and Cell Function in Human Skin Grafts Derived from Cryopreserved Allogeneic Dermis and Autologous Cultured Keratinocytes", The Journal of Investigative Dermatology, Nov. 1988, pp. 478-485, vol. 91, No. 5.
May, S. R., "The Future of Skin Banking", Journal of Burn Care & Rehabilitation, Sep.-Oct. 1990, vol. 11, No. 5, 484-486.
I.M. Leigh et al., "Skin Equivalents and Cultured Skin: From the Petri Dish to the Patient", Wounds: A Compendium of Clinical Research and Practice, Jul.-Aug. 1991, col. 3, No. 4, 141-148.
Heck et al., "Composite Skin Graft: Frozen Dermal Allografts Support the Engraftment and Expansion of Autologous Epidermis", J. Trauma, Feb. 1985, vol. 25, No. 2, 106-112.
English abstract of DE 195 13 177 (A1), Oct. 2, 1996.

(56) References Cited

OTHER PUBLICATIONS

Mackie, David P., "The Euro Skin Bank: Development and Application of Glycerol-Preserved Allografts," J Burn Care Rehabil, Jan./Feb. 1997, pp. S7-S9, vol. 18.
Lex, A., et al., "O uso de dura-mater homologa, conservada em glicerina, no tratamento das hernias incisionais", 77 Rev. Paul. Med., 123-128, Vo. 77, (1971).
Dias, A. R., et a;. "Avaliacao do comportamento da dura-mater humana quando submetida a diferentes agents conservadores", 22 Rev. Assoc. Med. Bras. 175-178, vol. 22., No. 78 (1976).
Pigossi, N., et al., Estudo experimental e clinico sobre o emprego, como implante, da dura mater homogena conservada em glicerina a temperatura ambiente, Brazilian med. Affairs, 263-278, vol. 17, No. 8, (1971).
Wainwright, D. et al., "Clinical Evaluation of an Acellular Allograft Dermal Matrix in Full-Thickness Burns", J. Burn Care & Rehabilitation, vol. 17, No. 2, 124-136 (Mar.-Apr. 1996).
Beard, J., "More ways devised for skin replacement", Houston Chronicle (Mar. 21, 1994).
Baird, J., "A Houston-area company has introduced an improved way to treat severe burns using specially processed skin from organ donors", Houston Chronicle (Dec. 14, 1993).
Mintz, B., "Revenues in the flesh: Skin graft product's demand grows", Houston Chronicle (Feb. 12, 1997).
"LifeCell Announces Study Finds Alloderm(R) Equivalent to 'Gold Standard' in Reconstructive Burn Surgery", Business Wire (Mar. 19, 1998).
Reichardt, L., et al., "Extracellular Matrix Molecules and Their Receptors: Functions in Neural Development," 14 Annual Review Neuroscience 531 (1991).
American Association of Tissue Banks: Standards for Tissue Banking (1996).
American Association of Tissue Banks: Standards for Tissue Banking (1998).
American Association of Tissue Banks: Technical Manual for Skin Banking (1992).
American Association of Tissue Banks: Technical Manual Musculoskeletal Tissues (1992).
Abstract of Ross, "Connective tissue cells, cell proliferation and synthesis of extracellular matrix—a review", Philospical Transactions Royal Society London B Bio Sci., Jul. 1975; 271(912): 247-59.
*LifeNet Health v. LifeCell Corporation*, Civil Action No. 2:13-CV-486, U.S. District Court for the Eastern District of Virginia, Opinion and Order, dated Jul. 18, 2014.
Docket Report for *LifeNet Health v. LifeCell Corporation*, Civil Action No. 2:13-CV-486, U.S. District Court for the Eastern District of Virginia, printed on Oct. 6, 2014.
Letter from G. Rubman dated Mar. 10, 2014 with attachment.
*LifeNet Health v. LifeCell Corporation*, Civil Action No. 2:13-CV-486, U.S. District Court for the Eastern District of Virginia, Transcript of proceedings PM Session, dated Nov. 3, 2014.
*LifeNet Health v. LifeCell Corporation*, Civil Action No. 2:13-CV-486, U.S. District Court for the Eastern District of Virginia, Transcript of proceedings AM Session, dated Nov. 7, 2014.
*LifeNet Health v. LifeCell Corporation*, Civil Action No. 2:13-CV-486, U.S. District Court for the Eastern District of Virginia, Transcript of proceedings PM Session, dated Nov. 6, 2014.
*LifeNet Health v. LifeCell Corporation*, Civil Action No. 2:13-CV-486, U.S. District Court for the Eastern District of Virginia, Transcript of proceedings AM Session, dated Nov. 14, 2014.
*LifeNet Health v. LifeCell Corporation*, Civil Action No. 2:13-CV-486, U.S. District Court for the Eastern District of Virginia, Transcript of proceedings PM Session, dated Nov. 13, 2014.
*LifeNet Health v. LifeCell Corporation*, Civil Action No. 2:13-CV-486, U.S. District Court for the Eastern District of Virginia, Transcript of proceedings PM Session, dated Nov. 17, 2014.
*LifeNet Health v. LifeCell Corporation*, Civil Action No. 2:13-CV-486, U.S. District Court for the Eastern District of Virginia, Transcript of proceedings PM Session, dated Nov. 7, 2014.
*LifeNet Health v. LifeCell Corporation*, Civil Action No. 2:13-CV-486, U.S. District Court for the Eastern District of Virginia, Transcript of proceedings PM session, dated Nov. 10, 2014.
*LifeNet Health v. LifeCell Corporation*, Civil Action No. 2:13-CV-486, U.S. District Court for the Eastern District of Virginia, Transcript of proceedings AM session, dated Nov. 12, 2014.
*LifeNet Health v. LifeCell Corporation*, Civil Action No. 2:13-CV-486, U.S. District Court for the Eastern District of Virginia, Transcript of proceedings PM session, dated Nov. 12, 2014.
*LifeNet Health v. LifeCell Corporation*, Civil Action No. 2:13-CV-486, U.S. District Court for the Eastern District of Virginia, Transcript of proceedings AM session, dated Nov. 13, 2014.
*LifeNet Health v. LifeCell Corporation*, Civil Action No. 2:13-CV-486, U.S. District Court for the Eastern District of Virginia, Transcript of proceedings held on Jan. 29, 2015.
Docket Report for *LifeNet Health v. LifeCell Corporation*, Civil Action No. 2:13-CV-486, U.S. District Court for the Eastern District of Virginia, printed on May 27, 2015.
*LifeNet Health v. LifeCell Corporation*, Civil Action No. 2:13-CV-486, U.S. District Court for the Eastern District of Virginia, Transcript of proceedings AM Session, dated Nov. 4, 2014.
*LifeNet Health v. LifeCell Corporation*, Civil Action No. 2:13-CV-486, U.S. District Court for the Eastern District of Virginia, Transcript of proceedings AM Session, dated Nov. 5, 2014.
*LifeNet Health v. LifeCell Corporation*, Civil Action No. 2:13-CV-486, U.S. District Court for the Eastern District of Virginia, Transcript of proceedings AM Session, dated Nov. 6, 2014.
*LifeNet Health v. LifeCell Corporation*, Civil Action No. 2:13-CV-486, U.S. District Court for the Eastern District of Virginia, Transcript of proceedings PM Session, dated Nov. 14, 2014.
*LifeNet Health v. LifeCell Corporation*, Civil Action No. 2:13-CV-486, U.S. District Court for the Eastern District of Virginia, Transcript of proceedings AM & PM Sessions, dated Nov. 18, 2014.
*LifeNet Health v. LifeCell Corporation*, Civil Action No. 2:13-CV-486, U.S. District Court for the Eastern District of Virginia, Transcript of proceedings PM Session, dated Nov. 5, 2014.
*LifeNet Health v. LifeCell Corporation*, Civil Action No. 2:13-CV-486, U.S. District Court for the Eastern District of Virginia, Transcript of proceedings AM Session, dated Nov. 3, 2014.
*LifeNet Health v. LifeCell Corporation*, Civil Action No. 2:13-CV-486, U.S. District Court for the Eastern District of Virginia, Transcript of proceedings PM Session, dated Nov. 4, 2014.
*LifeNet Health v. LifeCell Corporation*, Civil Action No. 2:13-CV-486, U.S. District Court for the Eastern District of Virginia, Transcript of proceedings AM session, dated Nov. 10, 2014.
*LifeNet Health v. LifeCell Corporation*, Civil Action No. 2:13-CV-486, U.S. District Court for the Eastern District of Virginia, Transcript of proceedings AM session, dated Nov. 17, 2014.
Docket Report for *LifeNet Health v. LifeCell Corporation*, Civil Action No. 2:13-CV-486, U.S. District Court for the Eastern District of Virginia, printed on Apr. 15, 2015.
George C. Na, "Interaction of Calf Skin Collagen with Glycerol: Linked Function Analysis", Biochemistry, 25, 1986, 967-73.

* cited by examiner

PLASTICIZED BONE AND SOFT TISSUE GRAFTS AND METHODS OF MAKING AND USING SAME

This application is a continuation application of U.S. application Ser. No. 12/701,634, filed Feb. 8, 2010, which is a continuation application of U.S. application Ser. No. 11/053,454, filed Feb. 9, 2005, which is a continuation application of U.S. application Ser. No. 09/940,545, filed Aug. 29, 2001, which is a divisional application of U.S. application Ser. No. 09/107,459, filed Jun. 30, 1998, now U.S. Pat. No. 6,293,970, all of which are hereby incorporated by reference in their entireties.

FIELD OF THE INVENTION

The present invention provides a plasticized dehydrated bone and/or soft tissue product that does not require special conditions of storage, for example refrigeration or freezing, exhibits materials properties that approximate those properties present in normal hydrated tissue, is not brittle and does not necessitate rehydration prior to clinical implantation. The invention replaces water in the molecular structure of the bone or soft tissue matrix with one or more plasticizers allowing for dehydration of the tissue, yet not resulting in an increase in brittleness of the plasticized product, and resulting in compressive and/or tensile properties similar to those of normal hydrated bone. Replacement of the chemical plasticizers by water prior to implantation is not required and thus, the dehydrated bone or soft tissue plasticized product can be placed directly into an implant site without significant preparation in the operating room. The present plasticized graft does not need rehydration, possesses adequate materials properties, and is not a potential source for disease transmission.

BACKGROUND OF THE INVENTION

Bone tissue is a homogeneous material comprised of osteoid and minerals. The osteoid is a viscous gel-like material comprised primarily of type I collagen (approximately 90%), proteoglycans, and various sulfated and non-sulfated mucopolysaccharides. The mineral component consists primarily of a crystalline form of calcium phosphate, hydroxy apatite, with amounts of calcium carbonate, tricalcium phosphate, and smaller amounts of other forms of mineral salts. This bone tissue is laid down around cells called osteocytes and these cells are found in small interconnected channels (lacunae) which are interconnected through a series of channels comprising the Haversian canal system. At the level of the microscope, it is possible to observe that bone tissue is organized into osteons of compact bone made of concentric, perivascular layers of highly coaligned mineralized collagen fiber bundles. The predominant orientation within a single layer varies with respect to the vascular axis and various combinations of orientation in successive lamellae result in variable overall collagen orientation within each osteon. Differences in overall collagen orientation are directly reflected in differing mechanical behavior of single osteons. Transversely oriented collagen results in better resistance to compressive loading along the axis, whereas predominant longitudinal orientation results in better resistance to tensile stress. The predominant orientation of collagen within a cross-section of long bone is not random, but matches the expected distribution of mechanical stress across the section, and its rotational shift along the whole shaft. More transverse collagen is deposited at sites of compressive loading, and more longitudinal collagen is deposited at sites of tensile stress. These structural oriented bone tissues in a load bearing bone are presumed to be laid down by the osteocytes present in the bone and bone remodeling mediates mechanical adaptation in compact bone.

A bone is typically comprised of bone tissue in the form of cortical and trabecular bone. Cortical bone is frequently referred to as compact bone and is the major load-bearing part of a bone. Trabecular bone is present in what is typically referred to as cancellous bone where it appears as a densely interconnected structure of "spongy" bone. Spongy bone in a typical bone contains the hemotopoietic cellular elements which is called bone marrow. Trabecular bone can be described as forming a cross-bracing lattice between cortical bone in a bone. It is important to emphasize a need to differentiate between "a bone" and "bone" (as a tissue). A bone is comprised of bone tissue present as cortical and cancellous (spongy) bone.

The mineralized osteoid typical of bone tissue is hydrated along the organic molecular structure and is an essential element of the mineral structure. Hydrating molecules of water form complex molecular associations with these organic and non-organic elements of bone tissue and can be described as being tightly bound, loosely bound, and free. Free water and loosely bound water can frequently be removed from bone tissue with only minor changes in the overall mechanical characteristics of the bone tissue. Tightly bound water can be removed only under extreme conditions and results in significant changes in the physical and mechanical properties of bone tissue. In fresh bone, water serves a solvating function in bone tissue allowing proper orientation and molecular spacing of the collagen fibrils which maintain structural alignment of the mineral phase in association with the organic phase.

Bone tissue in the form of bone grafts for implantation into a patient, is typically preserved and provided in a dehydrated state. Dehydration of bone tissue through drying, whether by air drying or sublimation as in freeze-drying, results in alteration of the molecular structure of the bone tissue and as a result of the reorientation of the collagen fibrils and the crystalline mineral phase, stress accumulates in the bone tissue. This stress can be relieved by rehydration or by the occurrence of small or large dislocations of structure. Small dislocations are designated micro fractures and are not usually visible to the naked eye. Large dislocations are designated fractures and are usually visible to the naked eye.

In a long bone, for example a femur, tibia, fibula, or humerus, the shaft separates the proximal and distal ends of the long bone. The shaft serves to focus loads applied to the whole bone into a smaller diameter than found at the proximal and distal ends of the long bone and the shaft of a long bone is typically of a cylindrical shape and is comprised of compact (cortical) bone. Loads applied along the axis of the shaft require that the cortical bone maintain a constant circumference, i.e. the tendency to failure would distort the bone tissue perpendicular to the axis of load application. Thus, the orientation of the collagen fibers should be such that tensile stress is resisted along the axis of loading and compressive stress is resisted perpendicular to loading. Drying of shaft portions of long bones results in reorientation of collagen fibers and the mineral phase such that changes in the circumferential orientation create stress within the bone matrix which can be relieved only by rehydration or occurrence of a fracture which allows a reorientation approximating the original orientation. In dehydrated cortical ring grafts cut from shafts of long bones, this stress release can present as a fracture along the long axis of the bone shaft leaving a circumference which approximates the circumference of the cortical ring graft prior to drying. By rehydrating bone grafts prior to implantation, the potential for fracture formation which can compromise the function of the bone product can be reduced, but not eliminated. Fractures as discussed above can occur in dehydrated bone prior to rehydration and result in a graft having compromised biomechanical properties, which in turn can result in graft failure when implanted in a patient.

Load-bearing soft tissue grafts such as ligaments, tendons, and fascia lata are frequently provided in a freeze-dried state. Such grafts must be rehydrated prior to clinical implantation. Such soft tissue grafts typically contain collagen, elastin, and assorted proteoglycans and mucopolysaccharides. The collagens and elastins are the load-bearing component(s) of these soft tissue grafts and the assorted proteoglycans and polysaccharides serve to bind the fibrillar collagens into a matrix-like structure. The structural organization of fascia lata is similar to dura mater in being somewhat isotropic in load-bearing properties (Wolfinbarger, L, Zhang, Y, Adam, BLT, Homsi, D, Gates, K, and Sutherland, V, 1994, "Biomechanical aspects on rehydrated freeze-dried human allograft dura mater tissues, J. Applied Biomaterials, 5:265-270) whereas tendons (for example the Achilles tendon) or ligaments (for example the Anterior cruciate ligament) are typically anisotropic in load-bearing properties. In these types of load-bearing soft tissue grafts, the tensile properties of the tissues depend on the flexibility of the collagenous structures to stretch under load and return to their original dimensions upon removal of the load.

A wide variety of bone and soft tissue products are used in veterinary, medical, orthopaedic, dental, and cosmetic surgery applications. These bone and soft tissue products can be used in load-bearing and non-load bearing applications and the bone and soft tissue products can be supplied under a variety of forms. Bone products are provided as fresh-frozen, freeze-dried, rehydrated freeze-dried, air-dried, organic solvent preserved, or provided preserved by other similar types of preservation methods. Each method of preservation of bone products possesses selected advantages and disadvantages and thus the method of preservation is generally modified to select for specific needs of a given bone graft. Soft tissue products are typically provided as fresh-frozen or freeze-dried and each method of preservation of soft tissue products possess selected advantages and disadvantages and thus the method of preservation is generally modified to select for specific needs of a given soft tissue product.

Bone and soft tissue products preserved and stored by methods involving freeze-drying (removal of water by sublimation) yield a bone or soft tissue product which is significantly more brittle than normal bone and has a tendency to fracture into numerous small pieces, which ultimately can result in graft failure. Specifically, freeze-drying causes grafts to be brittle and typically causes shrinkage where the shrinkage is often not uniform, thereby causing graft failure; solvent preservation using for example, acetone or alcohol, can cause irreversible denaturation of proteins, and solubilization of solvent soluble components, including for example, lipids. These alterations in materials properties of the bone and soft tissue products necessitates a rehydration step in preparation of the bone and soft tissue product for implantation. However, rehydration does not solve the problem, grafts can fracture prior to rehydration, thereby making rehydration futile, and if there are micro fractures prior to rehydration they remain after rehydration. These grafts are more likely to fail regardless of whether they are rehydrated. Even after rehydration the materials properties do not approximate the materials properties of normal bone.

Bone and soft tissue products are generally separated into load bearing and non-load bearing products. Examples of non-load bearing bone products are ground demineralized bone which are used for inducing new bone formation in a particular implant site. Load-bearing bone products are rarely demineralized and are used at implant sites where the bone graft will be expected to withstand some level of physical load(s). It is therefore important that load bearing bone products not fail during normal movement(s) of the implant recipient and that the bone product not stimulate a pronounced physiological response. The majority of bone products are provided in either the fresh-frozen or freeze-dried format. The fresh-frozen format is undesirable because it includes donor derived bone marrow and is thus immunogenic and a source of disease transmission. The freeze-dried format is less of a problem than fresh-frozen grafts in the potential for disease transmission, however a freeze-dried bone graft is significantly more brittle than normal bone, more brittle than fresh frozen bone, and must be rehydrated prior to clinical usage. In that clinicians typically do not have time to adequately rehydrate bone graft products in the operating room, it is advantageous to provide a dehydrated or freeze-dried bone product which does not need rehydration, possesses adequate materials properties, and is not a potential source for disease transmission.

SUMMARY OF THE INVENTION

It is an objective of the present invention to provide implantable, non-demineralized, load-bearing bone products which are mechanically stabilized in a dehydrated state by use of biocompatible plasticizers.

It is a further objective of the present invention to provide implantable, load-bearing, soft tissue products which are mechanically stabilized in a dehydrated state by use of biocompatible plasticizers.

It is also an objective of the present invention to provide implantable, load-bearing, bone products which do not require rehydration.

It is yet a further objective of the present invention to provide implantable, load-bearing, soft tissue products which do not require rehydration.

It is an objective of the present invention to provide methods of plasticizing load-bearing bone and soft tissue products.

It is a further objective of the present invention to provide plasticized bone and soft tissue products which are resistant to proliferation of microorganisms.

It is yet a further objective of the present invention to provide bone and soft tissue products which can be stored at room temperature using conventional packaging.

It is a further objective of the present invention to provide plasticized bone and soft tissue products where the plasticizer can be readily removed prior to implantation.

It is a further objective of the present invention to use plasticizers to plasticize bone and soft tissue products which are not toxic to a recipient of the plasticized bone or soft tissue graft.

It is yet a further objective of the present invention to provide implantable load-bearing bone and soft tissue products which are similar in physical, chemical, and biological properties as compared to normal tissue (fresh bone or fresh soft tissues) yet lack the inherent disadvantages (including for example, potential disease transmission, increased immunogenicity, and a tissue (e.g. bone marrow) which can yield toxic degradation products and/or retard graft incorporation) of fresh-frozen, dehydrated, and freeze-dried bone and/or soft tissue products.

It is a further objective of the present invention to provide a plasticized bone graft suitable for transplantation into a human, including a non-demineralized bone graft having an internal matrix essentially free from bone marrow elements; and one or more plasticizers contained in the internal matrix.

It is an object of the present invention to provide a plasticized bone graft, including a cleaned, non-demineralized, bone graft; and one or more plasticizers, where the cleaned non-demineralized bone graft is impregnated with the one or more plasticizers.

It is yet a further objective of the present invention to provide a plasticized bone graft, including a cleaned, non-demineralized, bone graft including one or more plasticizers.

It is a further objective of the present invention to provide a method for producing a plasticized bone graft suitable for transplantation into a human, by impregnating a cleaned, non-demineralized, bone graft with one or more plasticizers to produce a plasticized bone graft.

Plasticity of soft tissues depends primarily on the waters of hydration present in the matrix structure, where water movement under a load is restricted by the viscous nature of the proteoglycan/polysaccharide component, and bound waters of hydration in the collagen component affect the flexibility of the tensile component of the tissue(s). The present invention deals with the plasticization of these load bearing tissue constructs where the water removed is replaced with one or more plasticizers including for example, glycerol (glycerin USP) (liquid substitution) such that the graft does not need to be rehydrated or washed to remove the plasticizer prior to clinical implantation.

The present invention provides a dehydrated or freeze-dried plasticized bone or soft tissue product, preferably containing less than 5% residual moisture, which product requires no or minimal processing just prior to clinical implantation. The present invention solves prior art problems of grafts having insufficient materials properties, graft brittleness, and the necessity for rehydration prior to clinical implantation, by providing a plasticized dehydrated bone and/or soft tissue product that exhibits materials properties that approximate those properties present in normal hydrated tissue, is not brittle and does not necessitate rehydration prior to implantation.

DETAILED DESCRIPTION

I. Definitions

The below definitions serve to provide a clear and consistent understanding of the specification and claims, including the scope to be given such terms.

Alcohol. By the term "alcohol" is intended for the purposes of the present invention, one of a series of organic chemical compounds in which a hydrogen attached to carbon is replaced by a hydroxyl. Suitable alcohols useful in the plasticizer composition of the present invention preferably include $C_1$-$C_{10}$ alcohols, and more preferably ethanol and isopropyl alcohol.

Allowash™ Solution. By the term "Allowash™ Solution" is intended those detergent compositions disclosed in co-pending U.S. patent application Ser. No. 08/620,856 incorporated herein by reference. Examples of suitable Allowash compositions include: a cleaning composition containing essentially about 0.06 wt % polyoxyethylene-4-lauryl ether; about 0.02 wt % poly (ethylene glycol)-p-nonyl-phenyl-ether; about 0.02 wt % octyphenol-ethyleneoxide and endotoxin free deionized/distilled water.

Biocompatible. By the term "biocompatible" is intended for the purposes of the present invention, any material which does not provoke an adverse response in a patient. For example, a suitable biocompatible material when introduced into a patient does not itself provoke a significant immune response, and is not toxic to the patient.

Biomechanical strength. By the term "biomechanical strength" is intended for the purposes of the present invention, those properties exhibited by a tissue graft including loading strength, compressive strength, and tensile strength.

Bone graft. By the term "bone graft" is intended for the purposes of the present invention, any bone or piece thereof obtained from a donor for example a human or animal and/or cadaver donor, including for example any essentially intact bone graft including for example the femur, tibia, ilia, humorous, radius, ulna, ribs, whole vertebrae, mandibula and/or any bone which can be retrieved from a donor with minimal cutting of that bone for example, one half of an ulna, a femur cut in half to yield a proximal half and a distal half, femoral head, acetabula, distal femur, femur shaft, hemi-pelvi, humerus shaft, proximal femur, proximal femur with head, proximal humeri, proximal tibia, proximal tibia/plateaus, talus, tibia shaft, humeral head, ribs, and/or at least a substantial portion of a whole bone, i.e. at least one-quarter of a whole bone; and/or any cut bone grafts including for example an iliac crest wedge, a Cloward dowel, a cancellous cube, a fibular strut, cancellous block, a crock dowel, femoral condyles, femoral ring, femur segment, fibula segment, fibular wedge, tibia wafer, ilium strip, Midas Rex dowel, tibia segment, and radius/ulna wedge.

Bone marrow elements. By the term "bone marrow elements" is intended for the purposes of the present invention, the highly cellular hemotopoietic connective tissue filling the medullary cavities and spongy epiphysis of bones which may harbor bacterial and/or viral particles and/or fungal particles, and includes for example, blood and lipid.

Cleaned bone graft. By the term "cleaned bone graft" is intended for the purposes of the present invention, a bone graft that has been processed using means know in the art, to remove bone marrow elements.

Dehydrated bone or soft tissue. By the term "dehydrated bone or soft tissue" is intended bone tissue or soft tissue which is preserved by dehydration, such drying methods including for example, freeze-drying, and/or sublimation and/or air drying and/or liquid substitution.

Essentially free from. By the term "essentially free from" is intended for the purposes of the present invention, a bone graft where the material removed (i.e., bone marrow elements) from the bone graft is not detectable using detection means known in the art at the time of filing of this application.

Incubating. By the term "incubating" is intended for the purposes of the present invention, processing a bone graft in for example a plasticizer composition by soaking the graft in the composition, shaking the graft with the composition, subjecting the graft to flow of the composition where the flow is induced by negative or positive pressure, subjecting the graft and/or the composition to negative or positive pressure, or soaking the bone graft in a plasticizer composition in a negative pressure environment.

Impregnating. By the term "impregnating" is intended for the purposes of the present invention, any processing conditions which result in filling the internal matrix of a bone graft with a plasticizer composition.

Internal matrix. By the term "internal matrix" is intended for the purposes of the present invention, the spongy epiphysis of bones, the intercellular substance of bone tissue including collagen fibers and inorganic bone salts; or in soft tissue, the intercellular substance of such soft tissue including for example ligaments and tendons, including collagen and elastin fibers and base matrix substances.

Load-bearing. By the term "load-bearing" is intended for the purposes of the present invention a non-demineralized bone product or soft tissue product for implantation in a patient at a site where the bone graft or soft tissue graft will be expected to withstand some level of physical load(s).

Materials properties. By the term "materials properties" is intended for the purposes of the present invention, those properties present in normal fresh bone which include for example, loading strength, compressive strength, tensile strength, and deformability.

Negative pressure. By the term "negative pressure" is intended for the purposes of the present invention, a pressure below atmospheric pressure, i.e. below 1 atm.

Normal bone or soft tissue. By the term "normal bone or soft tissue" is intended for the purposes of the present invention, fresh hydrated autogenous and/or fresh-frozen hydrated allograft tissue including for example, bone, fascia, ligaments, and tendons.

Permeation enhancer. By the term "permeation enhancer" is intended for the purposes of the present invention, any agent including for example, isopropyl alcohol, that facilitates penetration of the one or more plasticizers or plasticizer composition into the bone or soft tissue. In the case of isopropyl alcohol, permeation is enhanced due to the reduced surface tension of the alcoholic solution.

Plasticization. By the term "plasticization" is intended for the purposes of the present invention, replacing free and loosely bound waters of hydration in a tissue(s) with one or more plasticizers without altering the orientation of the collagen fibers and associated mineral phase.

Plasticizer. By the term "plasticizer" is intended for the purposes of the present invention, any biocompatible compounds which are soluble in water and can easily displace/replace water at the molecular level and preferably have a low molecular weight such that the plasticizer fits into the spaces available to water within the hydrated molecular structure of the bone or soft tissue. Such plasticizers are preferably not toxic to the cellular elements of tissue into which the graft is to be placed, or alternatively, the plasticizer is easily removed from the graft product prior to implantation. Suitable plasticizers are preferably compatible with and preferably readily associates with the molecular elements of the bone tissue and/or soft tissue. Suitable plasticizers include for example: glycerol (glycerin USP), adonitol, sorbitol, ribitol, galactitol, D-galactose, 1,3-dihydroxypropanol, ethylene glycol, triethylene glycol, propylene glycol, glucose, sucrose, mannitol, xylitol, meso-erythritol, adipic acid, proline, hydroxyproline or similar water-soluble small molecular weight solutes which can be expected to replace water in the base matrix structure of bone tissue and/or soft tissue and provide the hydrating functions of water in that tissue. Suitable solvents include for example: water, alcohols, including for example ethanol and isopropyl alcohol.

Plasticizer composition. By the term "plasticizer composition" is intended for the purposes of the present invention, any composition which includes one or more plasticizers and one or more biocompatible solvents. Suitable solvents include for example: water, and alcohols, including for example $C_1$-$C_{10}$ alcohols, and more preferably ethanol and isopropyl alcohol.

Positive pressure. By the term "positive pressure" is intended for the purposes of the present invention, a pressure above atmospheric pressure, i.e. above 1 atm.

Rehydration. By the term "rehydration" is intended for the purposes of the present invention, hydrating a dehydrated plasticized tissue graft or a dehydrated non-plasticized tissue graft, with water, for example, prior to implantation into a patient. In the case of a plasticized graft, the plasticizer may optionally be not replaced by water or may optionally be partially or fully replaced by water.

Soft tissue grafts. By the term "soft tissue grafts" is intended for the purposes of the present invention, load-bearing and non-load-bearing soft tissue products. Non load-bearing grafts include cadaveric skin. Load-bearing soft tissue grafts include for example: pericardium, dura mater, fascia lata, and a variety of ligaments and tendons. Soft tissue grafts are composed of an internal matrix which includes collagen, elastin and high molecular weight solutes where during cleaning cellular elements and small molecular weight solutes are removed.

II. Plasticizers

Plasticization of load-bearing bone or soft tissue grafts represents a method of replacing free and loosely bound waters of hydration in the tissue(s) with a plasticizer composition containing one or more plasticizers, without altering the orientation of the collagen fibers and associated mineral phase. Suitable plasticizers include compounds which are soluble in water and can easily displace/replace water at the molecular level. Suitable plasticizers preferably have a low molecular weight such that the plasticizer fits into the spaces available to water within the hydrated molecular structure of the bone or soft tissue. Such plasticizers are not toxic to the cellular elements of tissue into which the graft is to be placed, or alternatively, the plasticizer is easily removed from the graft product prior to implantation. Finally, the plasticizer is preferably compatible with and preferably readily associates with the molecular elements of the bone or soft tissue.

Plasticizers suitable for use in the present invention include for example, a variety of biocompatible aqueous solutions. Examples of acceptable plasticizers include, but are not restricted to, members of the polyol family (sugar alcohols) of compounds including $C_2$ to $C_7$ polyols, monoglycerides (such as monoolein and monolinolein), and various short- and medium-chain free fatty acids (such short-chain free fatty acids preferably having a carbon chain length of less than six C, and such medium-chain free fatty acids preferably having a carbon chain length of from $C_{12}$ to $C_{14}$) and their corresponding monoacylglycerol esters (MGs) such as the saturated MGs, ranging in carbon chain length from $C_5$ to $C_{16}$, and preferably $C_5$ to $C_{14}$ MGs. Specific plasticizers include, but are not limited to, glycerol (glycerin USP), adonitol, sorbitol, ribitol, galactitol, D-galactose, 1,3-dihydroxypropanol, ethylene glycol, triethylene glycol, propylene glycol, glucose, sucrose, mannitol, xylitol, meso-erythritol, adipic acid, proline, hydroxyproline or similar water-soluble small molecular weight solutes which can be expected to replace water in the base matrix structure of bone or soft tissue, and provide the hydrating functions of water in that tissue. Other plasticizers suitable for use in the present invention can be readily selected and employed by one of ordinary skill in the art to which the present invention pertains without undue experimentation depending on the desired clinical outcome, sensitivity of the implantation procedure, patient sensitivities, and physician choice.

The present plasticizers are preferably employed at a concentration in the range of from 0.1 to 2.0 M, 10% to 100% by weight/volume, or 3% to 30% by weight of bone or soft tissue. The use of Molar concentrations and weight/volume percentages to express preferred concentration ranges are intended to deal with the concentrations of these plasticizers in the solutions used to treat the tissues. The use of the weight percent of plasticizer in load-bearing bone or soft tissue is intended to deal with the effective quantity of a given plasticizer in the load-bearing tissue which is necessary to effectively replace the waters of hydration present in the unprocessed tissues which are maximally plasticized to a state approximating normal tissue. The plasticizer can be introduced into the bone or soft tissue matrix at any number of steps in the processing procedures and at a variety of concentrations with and without the use of permeation enhancers.

The result(s) of plasticization of load-bearing bone and soft tissue products are bone or soft tissue products which are similar to traditionally dehydrated bone and soft tissue products in residual moisture but are not subject to fractures or micro fractures like such dehydrated products, yet do not need to be rehydrated prior to use. The mechanical and use properties of a plasticized bone or soft tissue product are similar to those of natural (fresh autogenous and/or fresh-frozen allograft) bone, dura, pericardium, fascia, ligaments, and tendons.

III. Graft Cleaning and Processing

The present plasticizers may be introduced to the bone or soft tissue products at several points in the processing procedure(s). Bone processing and cleaning procedures suitable for use with the present invention include known processes, as well as the processes described in U.S. Pat. No. 5,556,379 and co-pending U.S. patent application Ser. No. 08/871,601 "Process for Cleaning Grafts Using Centrifugal Force and Bone Grafts Produced Thereby"; Ser. No. 08/620,858 "Composition for Cleaning Bones"; Ser. No. 08/646,520 "Recirculation Method for Cleaning Essentially Intact Bone Grafts Using Pressure Mediated Flow of Solutions and Bone Grafts Produced Thereby"; and Ser. No. 08/646,519 "Ultrasonic Cleaning of Allograft Bone" which are hereby incorporated herein in their entirety. The plasticizers may be incorporated into the processing procedure(s) using steps where the plasticizer(s) is/are present at essentially fill strength, i.e. 100% concentration, in the presence and/or absence of permeation enhancers, and at concentrations less than fill strength.

Bone tissue is cleaned and processed as described in U.S. Pat. No. 5,556,379, and co-pending U.S. patent application Ser. Nos. 08/871,601; 08/620,858; 08/646,520; and 08/646,519 by for example, transection of an essentially intact bone or perforation of an essentially intact bone with attachment of sterile plastic tubing to the cut end of a transected bone or to an attachment port inserted into the perforation of the perforated bone. The bone is immersed in a cleaning solution, such solutions including known cleaning agents as well as those described in the above-identified patent and co-pending patent applications, with or without use of sonication. The cleaning solution is induced to flow into, through, and out of the bone through use of a peristaltic pump or negative pressure applied to the cleaning solution. The induced flow of cleaning solution draws the bone marrow from the interior of the bone, and particularly from the cancellous bone marrow space, where it can be safely deposited in a receiving container containing a strong virucidal agent such as sodium hypochlorite (common bleach). The cleaned bone can then be further cleaned by causing the cleaning solution to be replaced with a solution of one or more decontaminating agents, including for example 3% hydrogen peroxide, with or without plasticizer. Hydrogen peroxide which in addition to its mild disinfection activity generates oxygen bubbles that can further assist in dislodging residual bone marrow materials causing the residual bone marrow materials to flow from the bone and into the receiving container.

In the above-described process, after processing with the cleaning solution, after processing with a decontaminating agent, in place of processing with a decontaminating agent, or after dehydration, the cleaned graft is plasticized for example, by processing the cleaned graft with a plasticizer composition containing one or more plasticizers including for example glycerin USP in a solvent.

IV. Plasticization

Bone and soft tissue grafts can be cleaned and processed using conventional methods, including those described in. When processing using these methods the graft is plasticized by adding one or more plasticizers or a plasticizer composition to processing steps after bone cleaning is essentially completed, and prior to freeze-drying. Under freeze-drying, the water present in the bone (or smaller cut bone grafts produced form the essentially intact bone) is removed by sublimation, however, the glycerol will remain and replace the free and bound water as the water is removed from the bone tissue. The one or more plasticizer(s) is added to fully hydrated bone tissue and the plasticizer(s) are induced to penetrate into the bone tissue optionally using a permeation enhancer. Thus, the bone or soft tissue is dehydrated yet the materials properties of the bone tissue will be similar to the materials properties of normal bone or soft tissue, i.e. partially or fully hydrated bone or soft tissue. The produced plasticized bone or soft graft contains minimal quantities of the plasticizer(s) and can be removed from the package and directly implanted into a patient without rehydration. If the presence of these small quantities of glycerol is of concern, the bone or soft tissue grafts may be quickly rinsed and/or washed in sterile saline just prior to implantation.

Bone or soft tissue cleaned and processed by the methods as described for bone cleaning and processing in U.S. Pat. No. 5,556,379, and/or co-pending U.S. patent application Ser. Nos. 08/871,601; 08/620,858; 08/646,520; and/or 08/646,519 and/or bone or soft tissue cleaned and processed by conventional methods, may be plasticized by processing with the plasticizer composition containing one or more plasticizers, including for example glycerin USP, in a solvent by for example drawing the plasticizer composition into the bone. Suitable solvents include for example, 70% isopropyl alcohol. The 70% isopropyl alcohol/plasticizer composition can be prepared by diluting absolute (100%) isopropyl alcohol with the one or more plasticizers, including for example glycerin USP such that the plasticizer accounts for 30% of the total volume and isopropyl alcohol accounts for 70% of the total volume. Under this method, the original processing procedures as described in U.S. Pat. No. 5,556,379 regarding the use of 70% isopropyl alcohol, is retained essentially unchanged. The isopropyl alcohol facilitates penetration of the glycerol into the tissue by acting as a permeation enhancer and the glycerol more readily penetrates the tissue due to the reduced surface tension of the alcoholic solution. The induced flow of glycerol/isopropyl alcohol into, through, and out of for example, the essentially intact bone, further serves to remove residual cellular elements, for example bone marrow materials, if any. It also allows penetration of the glycerol/isopropyl alcohol solution into the most remote areas of the tissue, and facilitates a uniform distribution of the glycerol into the tissue. The isopropyl alcohol can be removed from the tissue by washing with a washing solution including sterile water, for example as described in U.S. Pat. No. 5,556, 379 following the alcohol processing step. Preferably, the washing solution includes glycerin USP (30% volume:volume). The washing solution facilitates removal of the isopropyl alcohol without removal of the glycerin USP. The cleaned and plasticized tissue can then be frozen and freeze-dried or dehydrated according to standard protocols.

Alternatively, bone or soft tissue grafts may be plasticized after cleaning and freeze-drying. For example, tissue can be processed and cleaned according to any method including known methods, or as described in U.S. Pat. No. 5,556,379 described above. After the sterile water wash the tissue (for example bone tissue) is cleaned of virtually all cellular elements (for example, bone marrow) present in the tissue and the cleaned tissue can be further processed into for example, small cut bone grafts, and dehydrated or freeze-dried (also called lyophilized) using standard methods well known to those skilled in the art. Freeze-dried or dehydrated tissue grafts preferably contain less than about 5% residual moisture, satisfying the definition of freeze-dried bone allografts as prescribed under Standards of the American Association of Tissue Banks.

Clean freeze-dried or dehydrated bone or soft tissue grafts are plasticized by processing the tissue graft with a plasticizer composition, suitable compositions including for example 70% isopropyl alcohol/30% glycerin USP or 100% glycerin USP. Due to the presence of air in the cancellous and cortical bone spaces, the plasticizer(s) may only penetrate into the bone tissue with which it is in physical contact. Suitable methods for achieving physical contact between the plasticizer and bone or soft tissue include those methods known to one of ordinary skill in the art to which the present invention pertains. The plasticizer composition can be induced to flow into the cancellous and cortical bone spaces of bone tissue, or soft tissue, thus achieving physical contact, by various known methods that can be readily selected and employed by one of ordinary skill in the art to which the present invention pertains without undue experimentation, and include for example, agitation of the a tissue with the plasticizer composition, application of a vacuum (5 to 500 mTorr) above the plasticizer. The vacuum induces the air trapped in the, for example cancellous and cortical bone spaces/tissue to exit and be carried off. As the trapped air is removed from the cancellous and cortical bone spaces/tissue, the plasticizer quickly moves into the spaces previously occupied by air greatly enhancing penetration of the plasticizer into the bone or soft tissue. The plasticizer fills the spaces previously occupied by the free and bound water restoring the tissue to a materials property similar to that materials property of the original fully or partially hydrated tissue (e.g. normal bone).

The present one or more plasticizers may be introduced to soft tissue products at several points in the processing procedures, but are preferably introduced prior to the freeze-drying or dehydrating step. By introducing plasticizers prior to freeze-drying or dehydrating, the derived soft tissue graft is in a freeze-dried/dehydrated state where the plasticizer is used to stabilize the matrix and load bearing components of the soft tissue graft such that the graft can be used without rehydration/reconstitution.

V. Transplantation into a Patient

Prior to transplantation into a patient, excess glycerol may optionally be removed from the plasticized bone or soft tissue graft using for example, the method described in co-pending U.S. patent application Ser. No. 08/871,601. Specifically, the plasticized grafts are placed into centrifuge vessels/containers and on top of inserts designed to keep the bone grafts off of the bottom of the containers. The grafts are then centrifuged at 1,000 to 2,000 revolutions per minute (rpm) for 10-20 minutes. The excess glycerol or similar plasticizer exits the grafts and collects in the bottom of the centrifuge containers away from the grafts. The plasticizer tightly associated with the molecular and chemical structure of the tissue will not exit the graft and the tissue will remain plasticized without retaining physically discernable quantities of plasticizer. The plasticized graft(s) may then be packaged directly or packaged in a packaging format which permits application of a vacuum to the container. The current value of using a packaging format which permits storage of grafts under vacuum lies in the ability to predict possible loss of sterility with loss of vacuum to the packaging.

Clinical usage of plasticized bone or soft tissue grafts includes direct implantation of the grafts without further processing following removal from the packaging, implantation following a brief washing in sterile isotonic saline to remove any remaining traces of plasticizer associated with the immediate surfaces of the grafts, or by implantation following an extended (approximately 1 hour) washing with sterile isotonic saline to remove as much plasticizer as possible. Under any of the above described further processing of grafts, the materials properties of the plasticized grafts resemble those materials properties of fully or partially hydrated natural tissue (i.e. normal bone or soft tissue). The produced plasticized graft does not need to be rehydrated prior to clinical implantation, yet retains the strength and compressive/tensile properties of natural tissue. Plasticized freeze-dried soft tissue grafts where the plasticizer is used to stabilize the matrix and load bearing components of the soft tissue graft, can also be directly implanted in a patient without rehydration/reconstitution.

Suitable surgical methods for implanting bone and soft tissue grafts into a patient are well known to those of ordinary skill in the art to which the present invention pertains, and such methods are equally applicable to implantation of the present plasticized grafts. Those of ordinary skill in the art to which the present invention pertains can readily determine, select and employ suitable surgical methods without undue experimentation.

Further details of the process of the invention are presented in the examples that follow:

EXAMPLE 1

Processing of a Frozen Distal Femur

A. Cleaning and Processing: A frozen distal femur is selected and all of the soft tissue and periosteum is removed using sharp dissection techniques and periosteal elevators. The graft is then transected to the desired length using a Stryker™ saw or band saw. Each bisected piece is not more than 30 cm in length and is straight and contains no bone fragments. The surface cartilage is then removed from the femoral condyle with either a scalpel blade, periosteal elevator, or osteotome. The processing instructions dictate leaving the cartilage "on" when appropriate. Using a ⅜" drill bit, the cut end of the shaft is drilled approximately 5 cm. The interior of the intramedullary canal is then thoroughly washed with the lavage system.

An intercalary fitting is then inserted by screwing the threaded, tapered end into the cut end of the graft. The vacuum tubing is assembled by securing one end of the tubing to the nipple end of the intercalary fitting. The other end of the tubing is secured to the piston driven pump. Finally, another section of vacuum tubing is secured to the other side of the piston pump. Approximately 4000 cc of a 1:100 dilution of the "Allowash™ Solution" is poured into the sterile flushing vessel. The "Allowash™ Solution" is prepared by adding 4 cc of cleaning reagent to 3996 cc of sterile water. The flushing vessel is labeled as "Allowash™ Solution." The open end of the second piece of vacuum tubing is placed into a graduated flask. The piston pump is set to "reverse" and the flow rate controller is set to 50%. The pump is turned on and at least 500 cc of the first solvent (Allowash™ Solution) is drawn to waste. Thereafter, the open end of the second piece of vacuum tubing is removed from the graduated flask and placed into the sterile flushing vessel. The drive is maintained in the "reverse" position at 50%. The Allowash Solution recirculates for a minimum of 15 minutes.

The 1:100 dilution of the Allowash™ Solution is then decanted and approximately 4 liters of 3% hydrogen peroxide is added to the flushing vessel. The piston pump is set to reverse and the flow rate controller is set to 50%. The pump is then turned on and at least 500 cc of the 3% hydrogen peroxide solution is drawn to waste. Thereafter, the open end of the second piece of vacuum tubing is removed from the graduated flask and placed it into the sterile flushing vessel. The drive is maintained in the reverse position at 50%. The hydrogen peroxide is then allowed to recirculate for a minimum of 15 minutes.

The hydrogen peroxide is then decanted and approximately 3980 cc of sterile water is added along with the entire contents of reconstituted vials of Bacitracin and Polymyxin B to the flushing vessel. The flushing vessel is clearly labeled "antibiotic." The piston pump is then set to reverse and the flow rate controller is set at 50%. The pump is turned on and at least 500 cc of antibiotic solution is drawn to waste. The open end of the second piece of vacuum tubing is removed from the graduated flask and placed into the sterile flushing vessel. The drive is maintained in the reverse position at 50%. The antibiotic solution is allowed to recirculate for a minimum of 15 minutes.

B. Plasticization: The antibiotic solution is then decanted and approximately 4 liters of 70% isopropyl alcohol/30% glycerin USP is added to the flushing vessel. The flushing vessel is clearly labeled as 70% IPA/30% glycerin USP. The piston pump is set to reverse and the flow rate controller is set to 50%. The pump is turned on and at least 500 cc of IPA/glycerin USP solution is drawn to waste.

The open end of the second piece of vacuum tubing is removed from the graduated flask and placed into the sterile flushing vessel. The drive is maintained in the reverse position and the flow controller is set to 50%. The EPA/glycerin USP is allowed to recirculate for a minimum of 30 minutes. The IPA/glycerin USP solution is decanted and 4 liters of 30% glycerin USP in sterile water is added to the flushing vessel. The flushing vessel is labeled as glycerin USP washing solution. The piston pump is set to reverse and the flow rate controller is set to 50%. The pump is turned on and at least 500 cc of washing solution is drawn to waste.

The open end of the second piece of vacuum tubing is removed from the graduated flask and placed into the sterile flushing vessel. The drive is maintained in the reverse position and the flow rate controller is set to 50%. The washing solution is allowed to recirculate for a minimum of 15 minutes. Thereafter, the bone graft is removed from the flushing vessel and processed for freeze-drying as per standard operating procedure.

EXAMPLE 2

Processing of a Frozen Distal Femur

A. Cleaning and Processing: A frozen distal femur is selected and all of the soft tissue and periosteum is removed using sharp dissection techniques and periosteal elevators. The graft is then transected to the desired length using a Stryker™ saw or band saw. Each bisected piece is not more than 30 cm in length and is straight and contains no bone fragments. The surface cartilage is then removed from the femoral condyle with either a scalpel blade, periosteal elevator, or osteotome. The processing instructions dictate leaving the cartilage "on" when appropriate. Using a ⅜" drill bit, the cut end of the shaft is drilled approximately 5 cm. The interior of the intramedullary canal is then thoroughly washed with the lavage system.

An intercalary fitting is then inserted by screwing the threaded, tapered end into the cut end of the graft. The vacuum tubing is assembled by securing one end of the tubing to the nipple end of the intercalary fitting. The other end of the tubing is secured to the piston driven pump. Finally, another section of vacuum tubing is secured to the other side of the piston pump. Approximately 4000 cc of a 1:100 dilution of the "Allowash™ Solution" is poured into the sterile flushing vessel. The "Allowash™ Solution" is prepared by adding 4 cc of cleaning reagent The flushing vessel is labeled as "Allowash™ Solution." The open end of the second piece of vacuum tubing is placed into a graduated flask. The piston pump is set to "reverse" and the flow rate controller is set to 50%. The pump is turned on and at least 500 cc of the first solvent (Allowash Solution) is drawn to waste. Thereafter, the open end of the second piece of vacuum tubing is removed from the graduated flask and placed into the sterile flushing vessel. The drive is maintained in the "reverse" position at 50%. The Allowash Solution recirculates for a minimum of 15 minutes.

B. Plasticization: The 1:100 dilution of the Allowash™ Solution is decanted and approximately 4 liters of 3% hydrogen peroxide/30% glycerin USP is added to the flushing vessel. The piston pump is set to reverse and the flow rate controller is set to 50%. The pump is turned on and at least 500 cc of the 3% hydrogen peroxide/glycerin USP solution is drawn to waste. The open end of the second piece of vacuum tubing is removed from the graduated flask and placed into the sterile flushing vessel. The drive is maintained in the reverse position. The hydrogen peroxide/glycerin USP is allowed to recirculate for a minimum of 15 minutes.

The hydrogen peroxide/glycerin USP is then decanted and approximately 3980 cc of sterile water is added along with the entire contents of reconstituted vials of Bacitracin and Polymyxin B prepared in a water solution of 30% glycerin USP, to the flushing vessel. The flushing vessel is clearly labeled "antibiotic." The piston pump is then set to reverse and the flow rate controller is set at 50%. The pump is turned on and at least 500 cc of antibiotic solution is drawn to waste. The open end of the second piece of vacuum tubing is removed from the graduated flask and placed into the sterile flushing vessel. The drive is maintained in the reverse position at 50%. The antibiotic solution is allowed to recirculate for a minimum of 15 minutes.

The antibiotic solution is then decanted and approximately 4 liters of 70% isopropyl alcohol/30% glycerin USP is added to the flushing vessel. The flushing vessel is clearly labeled as 70% IPA/30% glycerin USP. The piston pump is set to reverse and the flow rate controller is set to 50%. The pump is turned on and at least 500 cc of IPA/glycerin USP solution is drawn to waste.

The open end of the second piece of vacuum tubing is removed from the graduated flask and placed into the sterile flushing vessel. The drive is maintained in the reverse position and the flow controller is set to 50%. The IPA/glycerin USP is allowed to recirculate for a minimum of 30 minutes. The IPA/glycerin USP solution is decanted and 4 liters of 30% glycerin USP in sterile water is added to the flushing vessel. The flushing vessel is labeled as glycerin USP washing solution. The piston pump is set to reverse and the flow rate controller is set to 50%. The pump is turned on and at least 500 cc of washing solution is drawn to waste.

The open end of the second piece of vacuum tubing is removed from the graduated flask and placed into the sterile flushing vessel. The drive is maintained in the reverse position and the flow rate controller is set to 50%. The washing solution is allowed to recirculate for a minimum of 15 minutes. Thereafter, the bone graft is removed from the flushing vessel and processed for freeze-drying as per standard operating procedure.

EXAMPLE 3

Processing of a Frozen Distal Femur

A. Cleaning and Processing: A frozen distal femur is selected and all of the soft tissue and periosteum is removed using sharp dissection techniques and periosteal elevators. The graft is then transected to the desired length using a Stryker™ saw or band saw. Each bisected piece is not more than 30 cm in length and is straight and contains no bone fragments. The surface cartilage is then removed from the femoral condyle with either a scalpel blade, periosteal elevator, or osteotome. The processing instructions dictate leaving the cartilage "on" when appropriate. Using a ⅜" drill bit, the cut end of the shaft is drilled approximately 5 cm. The interior of the intramedullary canal is then thoroughly washed with the lavage system.

An intercalary fitting is then inserted by screwing the threaded, tapered end into the cut end of the graft. The vacuum tubing is assembled by securing one end of the tubing to the nipple end of the intercalary fitting. The other end of the tubing is secured to the piston driven pump. Finally, another section of vacuum tubing is secured to the other side of the piston pump. Approximately 4000 cc of a 1:100 dilution of the "Allowash™ Solution" is poured into the sterile flushing vessel. The "Allowash™ Solution" is prepared by adding 4 cc of cleaning reagent. The flushing vessel is labeled as "Allowash™ Solution." The open end of the second piece of vacuum tubing is placed into a graduated flask. The piston pump is set to "reverse" and the flow rate controller is set to 50%. The pump is turned on and at least 500 cc of the first solvent (Allowash Solution) is drawn to waste. Thereafter, the open end of the second piece of vacuum tubing is removed from the graduated flask and placed into the sterile flushing vessel. The drive is maintained in the "reverse" position at 50%. The Allowash Solution recirculates for a minimum of 15 minutes.

The 1:100 dilution of the Allowash™ Solution is then decanted and approximately 4 liters of 3% hydrogen peroxide is added to the flushing vessel. The piston pump is set to reverse and the flow rate controller is set to 50%. The pump is then turned on and at least 500 cc of the 3% hydrogen peroxide solution is drawn to waste. Thereafter, the open end of the second piece of vacuum tubing is removed from the graduated flask and placed it into the sterile flushing vessel. The drive is maintained in the reverse position at 50%. The hydrogen peroxide is then allowed to recirculate for a minimum of 15 minutes.

The hydrogen peroxide is then decanted and approximately 3980 cc of sterile water is added along with the entire contents of reconstituted vials of Bacitracin and Polymyxin B to the flushing vessel. The flushing vessel is clearly labeled "antibiotic." The piston pump is then set to reverse and the flow rate controller is set at 50%. The pump is turned on and at least 500 cc of antibiotic solution is drawn to waste. The open end of the second piece of vacuum tubing is removed from the graduated flask and placed into the sterile flushing vessel. The drive is maintained in the reverse position at 50%. The antibiotic solution is allowed to recirculate for a minimum of 15 minutes.

The antibiotic solution is then decanted and approximately 4 liters of 70% isopropyl alcohol (IPA) is added to the flushing vessel. The flushing vessel is labeled as 70% IPA. The piston pump is set to reverse and the flow rate controller is set to 50%. The pump is turned on and at least 500 cc of IPA solution is drawn to waste. The open end of the second piece of vacuum tubing is removed from the graduated flask and placed into the sterile flushing vessel. The drive is maintained in the reverse position and the flow controller is set to 50%. The IPA recirculates for a minimum of 15 minutes. The IPA solution is then decanted and 4 liters of sterile water is added to the flushing vessel. The flushing vessel is labeled as "washing solution." The piston pump is set to reverse and the flow rate controller is set to 50%. The pump is turned on and at least 500 cc of washing solution is drawn to waste.

The open end of the second piece of vacuum tubing is removed from the graduated flask and placed into the sterile flushing vessel. The drive is maintained in the reverse position and the flow rate controller is set to 50%. The washing solution recirculates for a minimum of 15 minutes. The bone graft is removed from the flushing vessel and processed for freeze-drying as per standard operating procedure.

B. Plasticization: The freeze-dried bone graft(s) are then placed into sterile glycerin USP such that they are totally immersed in the viscous glycerol. Vacuum (10 to 500 mTorr, preferably 100 to 200 mTorr) is applied to the container until bubbles cease to exit the bone graft (about 5 to 60 minutes depending on the size and configuration of the bone graft, preferably about 20 to 30 minutes). The bone graft(s) are then removed from the glycerin USP solution and placed into an appropriate centrifuge container on top of a graft support.

The bone graft(s) are centrifuged at about 1000 to 2000 rpm until the glycerol ceases to exit the bone graft and accumulate in the bottom of the centrifuge container (usually 5 to 60 minutes depending on the size and configuration of the bone graft, preferably about 5 to 15 minutes). The bone graft(s) are then removed from their respective centrifuge containers and packaged for distribution.

EXAMPLE 4

Processing Cloward Dowels

A. Cleaning and Processing: Graft material is selected and all of the soft tissue and periosteum is removed from the distal femur, proximal and distal tibia, and cartilage is removed from the site. The femur is transected 10-15 cm above the femoral condyles and the distal femoral condyles are bisected. Transect the proximal tibia 10-15 cm below the tibial plateau. The distal femur or proximal tibia is placed in a Pan-A-Vise™. This is accomplished by removing a section of the diaphysis, allowing the vise jaws to grip the tissue securely. The Cloward set (12, 14, 16, 18, or 20 mm) is then assembled: 1. Place the extractor assembly within the cutter shaft, 2. Screw the cutter assembly onto the shaft with the aid of the Cloward set wrench, 3. Screw the set-point onto the extractor assembly, 4. Insert the shaft of the Cloward set into the ⅜" variable speed drill and tighten the chuck with the key. The set-point is then placed and locked at the forward aspect of the cutter.

The apparatus is then placed on the tissue to be fashioned. Drilling is commenced at a moderate speed. After the set-point has made a deep cut in the tissue, and the teeth have begun to cut into the tissue, drilling is stopped, and the set-point apparatus is unlocked. Drilling is continued using the marks created as a guide.

The Cloward(s) are then removed from the tissue block. A Stryker™ saw or band saw is then used to remove the cut grafts after all have been cut. Any cartilage is then trimmed from the cortical face of the Cloward(s) using a scalpel and a #10 blade. The distal end of the graft is then trimmed perpendicular to the body of the graft with a band saw making sure the fashioned graft is at least 15 mm long. The Cloward(s) are cleansed using pulsatile water apparatus. If the surface marrow is not easily removed, dry spin the graft(s) at 2600 rpm for 3 minutes.

The Cloward(s) are then placed in a sterile container with hydrogen peroxide (3%) at 37 to 44° C. The container is sealed and the container is placed into the centrifuge. The centrifuge is then balanced. The grafts are then centrifuged at 2600 rpm for 15 minutes. The tissue is removed from the centrifuge and the rafts are placed into an ultrasonic cleaner. Equal volumes of Allowash™ Solution, hydrogen peroxide (3%), and antibiotics are added to the ultrasonic cleaner and sonicate the tissue at 37-44° C. for a minimum of 1 hour. Thereafter, the tissue is removed from the ultrasonic cleaner.

The mixture is decanted and a sterile glass container is filled with fresh 3% hydrogen peroxide. The grafts are then placed in the container, the top is sealed and the container is taken to the large ultrasonic cleaner. The grafts are then sonicated for 90 minutes. Thereafter, the grafts are incubated overnight at 37-44° C. (minimum of 6 hours, preferably 12 to 18 hours).

B. Plasticization: After incubation, the hydrogen peroxide is decanted and the basin is filled with 70% isopropyl alcohol/30% glycerin USP and the grafts are incubated at room temperature for a minimum of 30 minutes. Thereafter, the isopropyl alcohol/glycerin USP solution is decanted and the container is filled with warm 30% glycerin USP in water. The grafts are incubated for a minimum of 30 minutes. Methods of incubation include for example: soaking.

The glycerin solution is then decanted and the Cloward dowels are removed from the container. The Cloward dowels are then placed into a sterile container. The container is sealed and placed into the centrifuge. The centrifuge is balanced and the grafts are centrifuged for 3-5 minutes to dry, and the remaining solution is removed.

The width and length of the Cloward(s) are measured, raft identification numbers are assigned, and the information is recorded on the "Tissue Processing Log Worksheet". One graft is then placed into a glass, 120 cc bottle and the printed label is affixed with the unique numeric designator. This step is repeated until all deposits are bottled. The bottled grafts are either frozen and packaged, or frozen and freeze-dried and packaged.

EXAMPLE 5

Processing Cloward Dowels

A. Cleaning and Processing: Graft material is selected and all of the soft tissue and periosteum is removed from the distal femur, proximal and distal tibia, and cartilage is removed from the site. The femur is transected 10-15 cm above the femoral condyles and the distal femoral condyles are bisected. Transect the proximal tibia 10-15 cm below the tibial plateau. The distal femur or proximal tibia is placed in a Pan-A-Vise™. This is accomplished by removing a section of the diaphysis, allowing the vise jaws to grip the tissue securely. The Cloward set (12, 14, 16, 18, or 20 mm) is then assembled: 1. Place the extractor assembly within the cutter shaft, 2. Screw the cutter assembly onto the shaft with the aid of the Cloward set wrench, 3. Screw the set-point onto the extractor assembly, 4. Insert the shaft of the Cloward set into the ⅜" variable speed drill and tighten the chuck with the key. The set-point is then placed and locked at the forward aspect of the cutter.

The apparatus is then placed on the tissue to be fashioned. Drilling is commenced at a moderate speed. After the set-point has made a deep cut in the tissue, and the teeth have begun to cut into the tissue, drilling is stopped, and the set-point apparatus is unlocked. Drilling is continued using the marks created as a guide.

The Cloward(s) are then removed from the tissue block. A Stryker™ saw or band saw is then used to remove the cut grafts after all have been cut. Any cartilage is then trimmed from the cortical face of the Cloward(s) using a scalpel and a #10 blade. The distal end of the graft is then trimmed perpendicular to the body of the graft with a band saw making sure the fashioned graft is at least 15 mm long. The Cloward(s) are cleansed using pulsatile water apparatus. If the surface marrow is not easily removed, dry spin the graft(s) at 2600 rpm for 3 minutes.

B. Plasticization: The Cloward(s) are then placed in a sterile container with hydrogen peroxide (3%) and glycerin USP (30%) at 37 to 44° C. The container is sealed and the container is placed into the centrifuge. The centrifuge is then balanced. The grafts are then centrifuged at 2600 rpm for 15 minutes. The tissue is removed from the centrifuge and the grafts are placed into an ultrasonic cleaner. Equal volumes of Allowash™ Solution, hydrogen peroxide (3%), 30% glycerin USP, and antibiotics are added to the ultrasonic cleaner and the tissue is sonicated at 37-44° C. for a minimum of 1 hour. Thereafter, the tissue is removed from the ultrasonic cleaner.

The mixture is decanted and a sterile glass container is filled with fresh 3% hydrogen peroxide/30% glycerin USP. The grafts are then placed in the container, the top is sealed and the container is taken to the large ultrasonic cleaner. The grafts are then sonicated for 90 minutes.

Thereafter, the grafts are incubated overnight at 37-44° C. (minimum of 6 hours, preferably 12 to 18 hours).

After incubation, the hydrogen peroxide is decanted and the basin is filled with 70% isopropyl alcohol/30% glycerin USP and the grafts are incubated at room temperature for a minimum of 30 minutes. Thereafter, the isopropyl alcohol/glycerin USP solution is decanted and the container is filled with warm 30% glycerin USP in water. The grafts are incubated for a minimum of 30 minutes. Methods of incubation include for example: soaking and mild agitation.

The glycerin solution is then decanted and the Cloward dowels are removed from the container. The Cloward dowels are then placed into a sterile container. The container is sealed and placed into the centrifuge. The centrifuge is balanced and the grafts are centrifuged for 3-5 minutes to dry, and the remaining solution is removed.

The width and length of the Cloward(s) are measured, graft identification numbers are assigned, and the information is recorded on the "Tissue Processing Log Worksheet". One graft is then placed into a glass, 120 cc bottle and the printed label is affixed with the unique numeric designator. This step is repeated until all deposits are bottled. The bottled grafts are either frozen and packaged, or frozen and freeze-dried and packaged.

EXAMPLE 6

Processing Cloward Dowels

A. Cleaning and Processing: Graft material is selected and all of the soft tissue and periosteum is removed from the distal femur, proximal and distal tibia, and cartilage is removed from the site. The femur is transected 10-15 cm above the femoral condyles and the distal femoral condyles are bisected. Transect the proximal tibia 10-15 cm below the tibial plateau. The distal femur or proximal tibia is placed in a Pan-A-Vise™. This is accomplished by removing a section of the diaphysis, allowing the vise jaws to grip the tissue securely. The Cloward set (12, 14, 16, 18, or 20 mm) is then assembled: 1. Place the extractor assembly within the cutter shaft, 2. Screw the cutter assembly onto the shaft with the aid of the Cloward set wrench, 3. Screw the set-point onto the extractor assembly, 4. Insert the shaft of the Cloward set into the 3/8" variable speed drill and tighten the chuck with the key. The set-point is then placed and locked at the forward aspect of the cutter.

The apparatus is then placed on the tissue to be fashioned. Drilling is commenced at a moderate speed. After the set-point has made a deep cut in the tissue, and the teeth have begun to cut into the tissue, drilling is stopped, and the set-point apparatus is unlocked. Drilling is continued using the marks created as a guide.

The Cloward(s) are then removed from the tissue block. A Stryker™ saw or band saw is then used to remove the cut grafts after all have been cut. Any cartilage is then trimmed from the cortical face of the Cloward(s) using a scalpel and a #10 blade. The distal end of the graft is then trimmed perpendicular to the body of the graft with a band saw making sure the fashioned graft is at least 15 mm long. The Cloward(s) are cleansed using pulsatile water apparatus. If the surface marrow is not easily removed, dry spin the graft(s) at 2600 rpm for 3 minutes.

The Cloward(s) are then placed in a sterile container with hydrogen peroxide (3%) at 37 to 44° C. The container is sealed and the container is placed into the centrifuge. The centrifuge is then balanced. The grafts are then centrifuged at 2600 rpm for 15 minutes. The tissue is removed from the centrifuge and the grafts are placed into an ultrasonic cleaner. Equal volumes of Allowash™ Solution, hydrogen peroxide (3%), and antibiotics are added to the ultrasonic cleaner and sonicate the tissue at 37-44° C. for a minimum of 1 hour. Thereafter, the tissue is removed from the ultrasonic cleaner.

The mixture is decanted and a sterile glass container is filled with fresh 3% hydrogen peroxide. The grafts are then placed in the container, the top is sealed and the container is taken to the large ultrasonic cleaner. The grafts are then sonicated for 90 minutes. Thereafter, the grafts are incubated overnight at 37-44° C. (minimum of 6 hours, preferably 12 to 18 hours).

After incubation, the hydrogen peroxide is decanted and the basin is filled with 70% isopropyl alcohol and the grafts are incubated at room temperature for a minimum of 30 minutes. Thereafter, the isopropyl alcohol is decanted and the container is filled with warm sterile water. The grafts are incubated for a minimum of 30 minutes. Methods of incubation include for example: soaking and mild agitation.

The wash solution is then decanted and the Cloward dowels are removed from the container. The Cloward dowels are then placed into a sterile container. The container is sealed and placed into the centrifuge. The centrifuge is balanced. The grafts are then centrifuged for 3-5 minutes to dry and the remaining solution is removed.

The width and length of the Cloward(s) are measured, graft identification numbers are assigned, and the information is recorded on the "Tissue Processing Log Worksheet". One graft is then placed into a glass, 120 cc bottle and the printed label is affixed with the unique numeric designator. This step is repeated until all deposits are bottled. The bottled grafts are either frozen and packaged, or frozen and freeze-dried and packaged.

B. Plasticization: Viscous glycerol is then added to each bottle sufficient to cover the graft and vacuum (10 to 500 mTorr) is applied to each bottle until the air ceases to exit the grafts (usually 5-20 minutes depending on graft type). The grafts are then removed from the bottles and placed into a centrifuge container. The grafts are centrifuged for 15-30 minutes or until glycerol ceases to exit the grafts and accumulate in the space below the grafts. The bottled grafts are either packaged or placed under vacuum and packaged.

EXAMPLE 7

Processing Cloward Dowels

A. Cleaning and Processing: Graft material is selected and all of the soft tissue and periosteum is removed from the distal femur, proximal and distal tibia, and cartilage is removed from the site. The femur is transected 10-15 cm above the femoral condyles and the distal femoral condyles are bisected. Transect the proximal tibia 10-15 cm below the tibial plateau. The distal femur or proximal tibia is placed in a Pan-A-Vise™. This is accomplished by removing a section of the diaphysis, allowing the vise jaws to grip the tissue securely. The Cloward set (12, 14, 16, 18, or 20 mm) is then assembled: 1. Place the extractor assembly within the cutter shaft, 2. Screw the cutter assembly onto the shaft with the aid of the Cloward set wrench, 3. Screw the set-point onto the extractor assembly, 4. Insert the shaft of the Cloward set into the 3/8" variable speed drill and tighten the chuck with the key. The set-point is then placed and locked at the forward aspect of the cutter.

The apparatus is then placed on the tissue to be fashioned. Drilling is commenced at a moderate speed. After the set-point has made a deep cut in the tissue, and the teeth have begun to cut into the tissue, drilling is stopped, and the set-point apparatus is unlocked. Drilling is continued using the marks created as a guide.

The Cloward(s) are then removed from the tissue block. A Stryker™ saw or band saw is then used to remove the cut grafts after all have been cut. Any cartilage is then trimmed from the cortical face of the Cloward(s) using a scalpel and a #10 blade. The distal end of the graft is then trimmed perpendicular to the body of the graft with a band saw making sure the fashioned graft is at least 15 mm long. The Cloward(s) are cleansed using pulsatile water apparatus. If the surface marrow is not easily removed, dry spin the graft(s) at 2600 rpm for 3 minutes.

B. Plasticization: The Cloward(s) are then placed in a sterile container with hydrogen peroxide (3%)/glycerin USP 30% at 37 to 44° C. The container is sealed and the container is placed into the centrifuge. The centrifuge is then balanced. The grafts are then centrifuged at 2600 rpm for 15 minutes. The tissue is removed from the centrifuge and the grafts are placed into an ultrasonic cleaner. Equal volumes of Allowash™ Solution, hydrogen peroxide (3%), and antibiotics are added to the ultrasonic cleaner and sonicate the tissue at 37-44° C. for a minimum of 1 hour. Thereafter, the tissue is removed from the ultrasonic cleaner.

The mixture is decanted and a sterile glass container is filled with fresh 3% hydrogen peroxide. The grafts are then placed in the container, the top is sealed and the container is taken to the large ultrasonic cleaner. The grafts are then sonicated for 90 minutes. Thereafter, the grafts are incubated overnight at 37-44° C. (minimum of 6 hours, preferably 12 to 18 hours).

After incubation, the hydrogen peroxide is decanted and the basin is filled with 70% isopropyl alcohol/30% glycerin USP and the grafts are incubated at room temperature for a minimum of 30 minutes. Thereafter, the isopropyl alcohol/glycerin USP solution is decanted and the container is filled with warm 30% glycerin USP in sterile water. The grafts are incubated for a minimum of 30 minutes. Methods of incubation include for example: soaking and mild agitation.

The solution is then decanted and the Cloward dowels are removed from the container. The Cloward dowels are then placed into a sterile container. The container is sealed and placed into the centrifuge. The centrifuge is balanced. The grafts are then centrifuged for 3-5 minutes to dry and the remaining solution is removed.

The width and length of the Cloward(s) are measured, graft identification numbers are assigned, and the information is recorded on the "Tissue Processing Log Worksheet". One graft is then placed into a glass, 120 cc bottle and the printed label is affixed with the unique numeric designator. This step is repeated until all deposits are bottled. The bottled grafts are either frozen and packaged, or frozen and freeze-dried and packaged.

EXAMPLE 8

Processing of an Iliac Crest Wedge

A. Cleaning and Processing: The soft tissue, periosteum, and cartilage is removed from an ilium. The ilium is placed in a Pan-A-Vise™ by removing a section of the ilium, allowing the vise jaws to grip the tissue securely. A Stryker saw is assembled with parallel cutting blades (12, 14, 16, 18, or 20 mm). The set-point at the forward aspect of the cutter is placed and locked. The apparatus is placed on the tissue to be fashioned and cutting is begun at a moderate speed.

After the set-point has made a deep cut in the tissue, and the teeth have begun to cut into the tissue, cutting is stopped, and the set-point apparatus is checked. Cutting is continued using the marks created as a guide. A Stryker™ saw or band saw is then used to remove the cut grafts after all have been cut.

Any cartilage is trimmed from the cortical face of the grafts(s) using a scalpel and a #10 blade. The distal end of the graft perpendicular to the body of the graft is trimmed with a band saw making sure the fashioned graft is at least 15 mm long. The Grafts is then cleansed using a pulsatile water apparatus. If the surface marrow is not easily removed, the graft(s) is dry spun at 2600 rpm for 3 minutes.

B. Plasticization: The Iliac Crest Wedge(s) are then placed in a sterile container with hydrogen peroxide (3%) and glycerin USP (30%) at 37 to 44° C. The container is sealed and placed into the centrifuge. The centrifuge is balanced. The grafts are then centrifuged at 2600 rpm for 15 minutes. The tissue is removed from the centrifuge and the grafts are placed into the ultrasonic cleaner. Equal volumes of Allowash™ Solution, hydrogen peroxide (3%), glycerin USP (30%), and antibiotics are added to the ultrasonic cleaner, and the grafts are sonicated at 37-44° C. for a minimum of 1 hour.

The tissue is then removed from the ultrasonic cleaner. The mixture is decanted and a sterile glass container is filled with fresh 3% hydrogen peroxide/30% glycerin USP. The grafts are placed in the container, the top is sealed and the container is taken to a large ultrasonic cleaner. The grafts are sonicated for 90 minutes. Thereafter, the grafts are incubated overnight at 37-44° C. (minimum of 6 hours, preferably for 12 to 18 hours). Methods of incubation include for example: soaking and mild agitation.

The hydrogen peroxide/glycerin USP is then decanted and the basin is filled with 70% isopropyl alcohol/30% glycerin USP. The grafts are then incubated at room temperature for a minimum of 30 minutes. The isopropyl alcohol/glycerin USP solution is then decanted and the container is filled with warm 30% glycerin USP in water. The grafts are incubated for a minimum of 30 minutes.

The glycerin USP solution is then decanted and the Iliac Crest Wedges are removed from the container. The Iliac Crest Wedges are then placed into a sterile container. The container is sealed and placed into the centrifuge. The centrifuge is balanced and the grafts are centrifuged for 3-5 minutes to dry and the remaining solution is removed.

The width and length of the Wedges are measured, graft identification numbers are assigned, and the information is recorded on the "Tissue Processing Log Worksheet". One graft is then placed into a glass, 120 cc bottle and the printed label is affixed with the unique numeric designator. This step is repeated until all deposits are bottled. The bottled grafts are either frozen and packaged, or frozen and freeze-dried and packaged.

EXAMPLE 9

Processing of Fascia Lata

A. Cleaning and Processing: Any remaining muscle tissue is removed from the fascia lata. The fascia is placed with the subcutaneous layer uppermost, on a clean, drape towel. Using blunt dissection techniques, all of the fat and extraneous soft tissue is removed from the graft material. The graft is kept moist with sterile water to prevent desiccation during processing.

Any torn fibers are removed from the edges of the graft material, and a graft rectangular in shape is created. The graft(s) are then placed in a basin containing a 1:100 dilution of Allowash™ Solution or other surfactant(s) for at least 15 minutes. The basin is labeled as Allowash™ Solution. The time of exposure is recorded on the Tissue Processing Log Worksheet.

B. Plasticization: The graft(s) are placed into an empty basin labeled "Rinse". The graft(s) are rinsed three time with copious amounts of sterile water to remove any residual detergents. Any sterile water which accumulates in the Rinse basin is discarded The number of rinses is recorded on the Tissue Processing Log Worksheet. The fashioned graft(s) are then placed in the basin containing U.S.P. grade 70% isopropyl alcohol containing 30% glycerin USP for 2-5 minutes. The basin is labeled IPA/Glycerin. The time of exposure to the alcohol/glycerin USP solution is recorded in the Tissue Processing Log Worksheet.

The graft(s) are then placed into the basin containing the antibiotic solution in 30% glycerin USP for at least 15 minutes. The basin is labeled as Antibiotics/Glycerin USP. The exposure time to the antibiotics/glycerin USP is recorded on the Tissue Processing Log Worksheet. The graft(s) are then thoroughly soaked by immersing each deposit into sterile 30% glycerin USP in deionized/distilled water for a minimum of 5 minutes to remove excess antibiotics. Enough sterile glycerin USP solution is needed to cover the graft(s). The basin is labeled as Rinse. The time of exposure to the glycerin USP rinse solution is recorded on the Tissue Processing Log Worksheet.

The fashioned graft(s) are then placed on sterile fine mesh gauze, and the gauze is trimmed to just beyond the edges of the graft. The width and length of the graft(s) is measured to the nearest tenth of a centimeter. The graft(s) are assigned identification numbers and this information is recorded on the Tissue Processing Log Worksheet. The graft and gauze is then rolled into a tube and graft material is then placed into glass, 120 ml bottles, and the printed label is affixed with the unique numeric designator. This step is repeated until all deposits are bottled. The graft material is now ready for wrapping and freeze-drying or dehydrating.

EXAMPLE 10

Processing Pericardium

A. Cleaning and Processing: The pericardial tissue is rinsed of any blood or pericardial fluid in sterile water in the basin labeled Rinse. The pericardium is then placed on a clean drape towel. Using blunt dissection techniques, all of the fat and extraneous soft tissue is removed from the graft material. The graft is kept moist with sterile water to prevent desiccation during processing. Any torn fibers are removed from the edges of the graft material, and a graft rectangular in shape is created. The graft(s) are then placed in a basin containing a 1:100 dilution of Allowash Solution or other surfactant(s) for at least 15 minutes. The basin is labeled as Allowash™ Solution. The time of exposure is recorded on the Tissue Processing Log Worksheet.

The graft(s) are placed into an empty basin labeled "Rinse". The graft(s) are rinsed three time with copious amounts of sterile water to remove any residual detergents. Any sterile water which accumulates in the Rinse basin is discarded. The number of rinses is recorded on the Tissue Processing Log Worksheet. The fashioned graft(s) are then placed in the basin containing U.S.P. grade 70% isopropyl alcohol containing 30% glycerin USP for 2-5 minutes. The basin is labeled IPA/Glycerin. The time of exposure to the alcohol/glycerin USP solution is recorded in the Tissue Processing Log Worksheet.

The graft(s) are then placed into the basin containing the antibiotic solution in 30% glycerin USP for at least 15 minutes. The basin is labeled as Antibiotics/Glycerin USP. The exposure time to the antibiotics/glycerin USP is recorded on the Tissue Processing Log Worksheet. The graft(s) are then thoroughly soaked by immersing each deposit into sterile 30% glycerin USP in deionized/distilled water for a minimum of 5 minutes, preferably from 10 to 15 minutes, to remove excess antibiotics. Enough sterile glycerin USP-solution is needed to cover the graft(s). The basin is labeled as Rinse. The time of exposure to the glycerin USP rinse solution is recorded on the Tissue Processing Log Worksheet.

The fashioned graft(s) are then placed on sterile fine mesh gauze, and the gauze is trimmed to just beyond the edges of the graft. The width and length of the graft(s) is measured to the nearest tenth of a centimeter. The graft(s) are assigned identification numbers and this information is recorded on the Tissue Processing Log Worksheet. The graft and gauze is then rolled into a tube and graft material is then placed into glass, 120 ml bottles, and the printed label is affixed with the unique numeric designator. This step is repeated until all deposits are bottled. The graft material is now wrapped and placed in a freeze dryer or dehydrated.

All of the publications and patent applications cited herein are hereby incorporated by reference into the present disclosure. It will be appreciated by those skilled in the art that various modifications can be made without departing from the essential nature thereof. It is intended to encompass all such modifications within the scope of the appended claims.

The invention claimed is:

1. A soft tissue graft, comprising:
   soft tissue obtained from a human or animal donor; and
   a plasticizer composition comprising one or more alcohols, wherein cellular elements are substantially removed from said soft tissue, and said plasticizer composition is contained in said soft tissue.

2. The graft of claim 1, wherein said one or more alcohols comprise ethanol or isopropyl alcohol.

3. The graft of claim 1, wherein said one or more alcohols comprise ethanol.

4. The graft of claim 1, wherein said soft tissue comprises one of cadaveric skin, pericardium, dura mater, fascia lata, ligaments, or tendons.

5. The graft of claim 1, wherein said soft tissue comprises cadaveric skin.

6. The graft of claim 1, wherein said soft tissue comprises human cadaveric skin.

7. The graft of claim 1, wherein said soft tissue graft is suitable to be stored at room temperature prior to transplantation into a human recipient.

8. The graft of claim 1, wherein said one or more alcohols comprise glycerol, adonitol, sorbitol, ribitol, galactitol, 1,3-dihydroxypropanol, ethylene glycol, triethylene glycol, propylene glycol, mannitol, xylitol, or mesoerythritol.

9. A method for producing a soft tissue graft, comprising:
   substantially removing cellular elements from soft tissue obtained from a human or animal donor;
   impregnating the soft tissue with a biocompatible, water-soluble plasticizer composition comprising one or more alcohols.

10. The method of claim 9, wherein said one or more alcohols comprise ethanol or isopropyl alcohol.

11. The method of claim 9, wherein said one or more alcohols comprise ethanol.

12. The method of claim 9, wherein the graft is suitable for transplantation after storage at room temperature.

13. The method of claim 9, wherein said soft tissue comprises cadaveric skin, pericardium, dura mater, fascia lata, ligaments, or tendons.

* * * * *